(12) United States Patent
Ishii

(10) Patent No.: US 8,203,709 B2
(45) Date of Patent: Jun. 19, 2012

(54) IMAGE OBTAINING METHOD AND IMAGE OBTAINING APPARATUS

(75) Inventor: Shuichi Ishii, Saitama (JP)

(73) Assignee: Fujifilm Corporation, Tokyo (JP)

( * ) Notice: Subject to any disclaimer, the term of this patent is extended or adjusted under 35 U.S.C. 154(b) by 322 days.

(21) Appl. No.: 12/561,171

(22) Filed: Sep. 16, 2009

(65) Prior Publication Data

US 2010/0067002 A1 Mar. 18, 2010

(30) Foreign Application Priority Data

Sep. 17, 2008 (JP) .................................. 2008-238090
Sep. 17, 2008 (JP) .................................. 2008-238091

(51) Int. Cl.
*G01J 3/28* (2006.01)
(52) U.S. Cl. ......... 356/326; 356/407; 382/162; 382/163
(58) Field of Classification Search .................. 356/326, 356/407; 600/160, 178; 382/162–163; 250/458.1, 250/459.1
See application file for complete search history.

(56) References Cited

U.S. PATENT DOCUMENTS

| | | | |
|---|---|---|---|
| 5,833,617 A | 11/1998 | Hayashi | |
| 7,583,993 B2 | 9/2009 | Sendai | |
| 7,646,002 B2 * | 1/2010 | Sendai | 250/461.2 |
| 2002/0177780 A1 | 11/2002 | Sendai | |
| 2003/0216626 A1 | 11/2003 | Tsujita et al. | |
| 2006/0211915 A1 | 9/2006 | Takeuchi et al. | |
| 2007/0015963 A1 | 1/2007 | Fengler et al. | |
| 2007/0183162 A1* | 8/2007 | Higuchi | 362/458 |
| 2007/0232861 A1* | 10/2007 | Kohno et al. | 600/160 |

FOREIGN PATENT DOCUMENTS

| | | |
|---|---|---|
| EP | 1256310 A2 | 11/2002 |
| EP | 1698272 A2 | 9/2006 |
| EP | 1705477 A2 | 9/2006 |
| EP | 1839561 A1 | 10/2007 |
| JP | 2003-93336 | 4/2003 |
| WO | WO 2006/116847 A1 | 11/2006 |

OTHER PUBLICATIONS

European Search Report dated Jan. 19, 2010.

* cited by examiner

*Primary Examiner* — Layla Lauchman
(74) *Attorney, Agent, or Firm* — McGinn IP Law Group, PLLC

(57) ABSTRACT

Emitting illumination light and auxiliary light having a wavelength range different from that of the illumination light onto an observation target simultaneously, obtaining an image formed of reflection light of the illumination light and reflection light of the auxiliary light reflected from the observation target, calculating, with respect to each pixel of the obtained image signal, estimated spectroscopic data in the wavelength range of the auxiliary light using a value of the image signal and estimated matrix data in the wavelength range of the auxiliary light stored in advance, obtaining quasi reflectivity information reflecting a reflectivity of the observation target in the wavelength range of the auxiliary light based on the estimated spectroscopic data in the wavelength range of the auxiliary light, and generating a special image based on the quasi reflectivity information.

5 Claims, 14 Drawing Sheets

FIG.21

| PSEUDO FLUORESCENCE YIELD F \ REFERENCE LIGHT INTENSITY E | $E_1$ | $E_2$ | $E_3$ | $E_4$ | $E_5$ |
|---|---|---|---|---|---|
| F1 | $(R_{11}, G_{11}, B_{11})$ ..... | $(R_{12}, G_{12}, B_{12})$ ........... | $(R_{13}, G_{13}, B_{13})$ ........... | $(R_{14}, G_{14}, B_{14})$ ........... | $(R_{15}, G_{15}, B_{15})$ ........... |
| F2 | $(R_{21}, G_{21}, B_{21})$ | | | | |
| F3 | | | $(R_{33}, G_{33}, B_{33})$ ........... | | |
| F4 | | | | | |
| F5 | $(R_{51}, G_{51}, B_{51})$ | | | | |

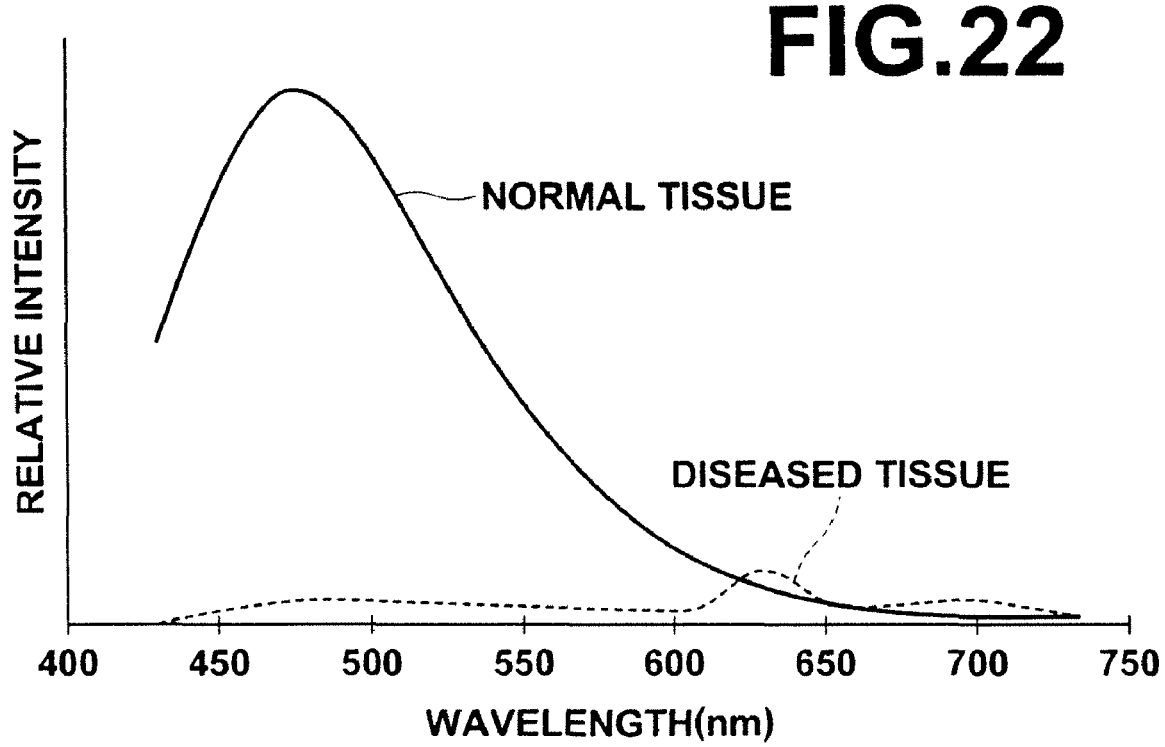

IMAGE OBTAINING METHOD AND IMAGE OBTAINING APPARATUS

BACKGROUND OF THE INVENTION

1. Field of the Invention

The present invention relates to an image obtaining method and apparatus for emitting illumination light and auxiliary light, and obtaining an image formed of reflection light of the illumination light and reflection light of the auxiliary light reflected from the observation target.

The invention also relates to an image obtaining method and apparatus for obtaining an image of an observation target irradiated with illumination light and excitation light simultaneously, which is formed of reflection light of the illumination light reflected from the observation target and fluorescence emitted from the observation target excited by the excitation light, and generating an ordinary image signal from the obtained image signal.

2. Description of the Related Art

Endoscope systems for observing tissues of body cavities have been widely known and electronic endoscope systems, in which an ordinary image is obtained by imaging an observation target in a body cavity illuminated by while light and the ordinary image is displayed on a monitor screen, have been widely put into practical use.

Recently, in the filed of electronic endoscope system using a solid state image sensor, a system that performs spectroscopic imaging by combining narrow band-pass filters based on a spectral reflectivity of a digestive organ, such as gastric mucosa, that is, an electronic endoscope system having narrow band-pass filters built therein (Narrow Band Imaging—NBI) has received attention. The system forms a spectroscopic image by employing narrow (wavelength) band-pass filters instead of a frame sequential rotating filter of R (red), G (green), and B (blue), sequentially outputting illumination light through the narrow band-pass filters, and processing the signals obtained by the illumination light beams in the same manner as in R, G, B (RGB) signal by changing the weighting on the signal. According to such a spectroscopic image, a microstructure or the like which has not been obtainable heretofore may be extracted from a digestive organ, such as stomach, large intestine, or the like.

In the mean time, unlike the frame sequential method that uses the narrow band-pass filters described above, in the simultaneous method in which microscopic mosaic color filters are arranged on the solid-state image sensor, Japanese Unexamined Patent Publication Nos. 2003-093336 and U.S. Patent Application Publication No. 20070183162 propose a method for forming a spectroscopic image by calculation based on an image signal obtained by imaging an observation target irradiated with white light. Japanese Unexamined Patent Publication No. 2003-093336 discloses a method for obtaining spectroscopic data of an observation target which do not depend on the type of illumination light, intrinsic spectroscopic property of the imaging system, and the like by obtaining estimated matrix data taken into account the spectroscopic property of the illumination light and the spectroscopic property of the entire imaging system including the color sensitivity characteristic of the image sensor, transmission factors of the color filters, and the like and performing calculation between RGB image signal obtained by the image sensor and the estimated matrix data.

Recently, in addition to the system of observing an observation target by emitting white light onto the target, the development of another type of image obtaining system has recently been underway. In this type of system, a medical agent that absorbs a predetermined wavelength, for example, ICG (indocyanine green) is administered to the observation target, then auxiliary light, which is light having a wavelength that the medical agent absorbs, is emitted to the observation target, and an image formed of reflection light of the auxiliary light reflected from the observation target is obtained, whereby a special image for observing the distribution of the medical agent in the observation target is generated.

Further, fluorescence image obtaining systems used as fluorescence endoscope systems are known, in which a fluorescence image is obtained by receiving autofluorescence emitted from an observation target irradiated with excitation light and the fluorescence image is displayed on a monitor screen together with the ordinary image described above. Such autofluorescence is emitted from an intrinsic phosphor in a living tissue. For example, if the observation target is an airway mucosa, it is thought that most of the autofluorescence is emitted from a lower layer of the mucosa, and the intrinsic phosphor can be riboflavin, tryptophan, tyrosine, NADH, NADPH, porphyrin, collagen, elastin, fibronectin, FAD, or the like.

Still further, it is known that, when excitation light in a given wavelength range is emitted onto an observation target, such as a living tissue, the light intensity/spectral shape of autofluorescence emitted from an phosphor inherent to the observation target differs between autofluorescence emitted from a normal tissue and autofluorescence emitted from a diseased tissue, as shown in FIG. 22. Fluorescence endoscope systems that make use of this phenomenon and generate a fluorescence image by emitting excitation light of a predetermined wavelength onto an observation target and detecting autofluorescence emitted from the observation target are also known. The reason why the autofluorescence emitted from the diseased tissue is attenuated more in comparison with the autofluorescence emitted from the normal tissue, as shown in FIG. 22, is presumed to be thickened mucosal epithelium of the diseased tissue, consumption of the intrinsic phosphor in the diseased tissue, or increase in the fluorescence absorbing material.

Further, as such type of fluorescence image obtaining system, for example, a fluorescence image obtaining system for generating a fluorescence image by administering a photosensitive material (ATX-S10, 5-ALA, Npe6, HAT-D01, Photofrin-2, or the like) having tumor-affinity and emits fluorescence when excited by light to a subject in advance as a luminous agent so as to be absorbed by a tumor, such as cancer, emitting excitation light with a wavelength corresponding to the excitation wavelength region of the luminous agent to the tumor, and detecting agent fluorescence emitted from the luminous agent collected in the tumor is also known.

In these fluorescence image obtaining systems, various types of comparative analysis methods have been proposed to allow an observer to accurately obtain information of tissue characteristics based on the fluorescence information. For example, when emitting excitation light onto an observation target, such as a living tissue, to obtain the light intensity of autofluorescence emitted from the observation target as a fluorescence image and displaying obtained fluorescence information based on the fluorescence image, the intensity of fluorescence emitted from a normal observation target is substantially proportional to the illuminance of excitation light, but the illuminance of excitation light decreases in inversely proportional to the square of the distance. Consequently, there may be a case in which fluorescence stronger than that of a normal tissue located remote from the light source is received from a diseased tissue located near the light source. Thus, an accurate determination of tissue characteristics of the observation target can not be made only with fluorescence intensity information.

In order to alleviate such problem, U.S. Patent Application Publication No. 20030216626 proposes a fluorescence image obtaining system for diagnosing tissue characteristics of a living body by emitting light having a wavelength range different from that of the excitation light onto an observation target as reference light, detecting the intensity of reflection light of the reference light reflected from the observation target, obtaining diagnostic information indicating a lesion site based on a fluorescence yield represented by the ratio between the fluorescence intensity and reflection light intensity of the reference light, and displaying the area of the lesion site, i.e., the diagnostic information, on the display screen of the fluorescence image in a different color, such as red.

Generally, in the image obtaining systems described above, acquisition of a special image by the emission of only auxiliary light onto an observation target or acquisition of a fluorescence image by the emission of excitation light onto the observation target and acquisition of an ordinary image by the emission of illumination light are performed in a time division manner. Then, a superimposed image is generated, for example, by superimposing the special image (or fluorescence image) on the ordinary image, and the superimposed image is displayed. When the special image (or fluorescence image) and ordinary image are obtained in the time division manner, however, the numbers of frames per unit time of the special image (or fluorescence image) and ordinary image are reduced, causing a problem that a favorable display image is not obtained when displaying the special image (or fluorescence image) as a moving picture.

Consequently, the inventor of the present invention has been engaging in the development of an image obtaining apparatus in which illumination light and auxiliary light (or excitation light) are emitted onto an observation target simultaneously, then an image formed of refection light of the illumination light and reflection light of the auxiliary light (or fluorescence) is obtained, and a special image reflecting a medical agent distribution in the observation target (or a fluorescence image reflecting a fluorescence emission intensity) from an image signal of the image.

The present invention has been developed in view of the circumstances described above, and it is an object of the present invention to provide an image obtaining method and apparatus capable of generating a favorable display image even where a special image (or a fluorescence image) is obtained by emitting illumination light and auxiliary light (or excitation light) onto an observation target simultaneously and based on reflection light of the auxiliary light (or fluorescence), and the special image (or fluorescence image) is displayed.

Further, when a fluorescence image of an observation target is observed, it is often the case that the user desires to observe an ordinary color image at the same time in order to make a comparison with the fluorescence image.

The present invention has been developed in view of the circumstances described above, and it is a further object of the present invention to provide an image obtaining method and apparatus capable of generating a quasi ordinary image signal having a low content rate of image signal attributable to fluorescence in an image obtaining method and apparatus in which illumination light and excitation light are emitted onto an observation target simultaneously to obtain an image formed of the reflection light and fluorescence.

SUMMARY OF THE INVENTION

An image obtaining method of the present invention is a method including the steps of:

emitting illumination light and auxiliary light having a wavelength range different from that of the illumination light onto an observation target simultaneously;

obtaining an image formed of reflection light of the illumination light and reflection light of the auxiliary light reflected from the observation target;

calculating, with respect to each pixel of the obtained image signal, estimated spectroscopic data in the wavelength range of the auxiliary light using a value of the image signal and estimated matrix data in the wavelength range of the auxiliary light stored in advance;

obtaining quasi reflectivity information reflecting a reflectivity of the observation target in the wavelength range of the auxiliary light based on the estimated spectroscopic data in the wavelength range of the auxiliary light, and generating a special image based on the quasi reflectivity information.

Preferably, a medical agent that absorbs light having the wavelength of the auxiliary light is administered to the observation target.

An image obtaining apparatus of the present invention is an apparatus, including:

a light emitting unit for emitting illumination light and auxiliary light having a wavelength range different from that of the illumination light onto an observation target simultaneously;

an imaging unit for obtaining an image formed of reflection light of the illumination light and reflection light of the auxiliary light reflected from the observation target;

a storage unit for storing at least estimated matrix data for calculating estimated spectroscopic data in the wavelength of the auxiliary light;

an estimated spectroscopic data calculation unit for calculating, with respect to each pixel of the image signal outputted from the imaging unit, estimated spectroscopic data in the wavelength range of the auxiliary light using a value of the image signal and estimated matrix data in the wavelength range of the auxiliary light; and an image processing unit for obtaining, with respect to each pixel, quasi reflectivity information reflecting a reflectivity of the observation target in the wavelength range of the auxiliary light based on the estimated spectroscopic data in the wavelength range of the auxiliary light, and generating a special image based on the quasi reflectivity information.

The term "auxiliary light having a wavelength range different from that of the illumination light" as used herein refers to that the wavelength range of the auxiliary light does not overlap with the wavelength range of the illumination light. Further, the term "estimated matrix data for calculating estimated spectroscopic data in the wavelength of the auxiliary light" as used herein refers to matrix data taken into account the spectroscopic property of the auxiliary light and the spectroscopic property of the imaging unit and allow estimated spectroscopic data that includes estimated spectral reflectivity information of the observation target in the wavelength range of the auxiliary light to be calculated by performing a matrix operation with an image signal.

If the light emitting unit is a unit that emits reference light having a wavelength range different from that of the auxiliary light onto the observation target simultaneously with the emission of the auxiliary light and the imaging unit is a unit that obtains an image that includes reflection light of the reference light reflected from the observation target, the image processing unit may be a unit that calculates a reference light intensity, which is an intensity of the reflection light of the reference light, from the image signal outputted from the imaging unit, and calculates the reflectivity information by dividing the estimated spectroscopic data in the wavelength range of the auxiliary light by the reference light intensity.

The term "reference light" as used herein may be light having a wavelength range different from that of the illumination light, for example, IR light or the like, or light included in the wavelength range of the illumination light. Where the wavelength range of the reference light is included in the wavelength range of the illumination light, the entire illumination light or light of a part of the wavelength range of the illumination light may be used as the reference light (the same applies hereinafter).

Further, for example, if light in the red region of the illumination light is used as the reference light, the light intensity of R image signal in RGB image signal may be used as "reference light intensity". If light of a predetermined wavelength in the illumination light is used as the reference light, estimated spectroscopic data in the wavelength range of the reference light may be calculated using an image signal of the illumination light and the estimated matrix data, and the calculated estimated spectroscopic data may be used as the "reference light intensity".

The image processing unit may be a unit that compares the quasi reflectivity information to a predetermined reference value, increases the estimated spectroscopic data in the wavelength range of the auxiliary light if the quasi reflectivity information is greater than the reference value, and generates the special image based on the increased estimated spectroscopic data in the wavelength range of the auxiliary light.

Further, the image processing unit may be a unit that compares the quasi reflectivity information to a predetermined reference value, increases the estimated spectroscopic data in the wavelength range of the auxiliary light if the quasi reflectivity information is smaller than the reference value, and generates the special image based on the increased estimated spectroscopic data in the wavelength range of the auxiliary light.

Still further, the image processing unit may be a unit that compares the quasi reflectivity information to a predetermined reference value and, if the quasi reflectivity information is smaller than the reference value, generates the special image by setting a saturated value as an RGB image signal.

The image processing unit may be a unit that generates a special superimposed image by superimposing the special image on an image generated based on the image signal outputted from the imaging unit.

Another image obtaining method of the present invention is a method, including the steps of:

obtaining an image of an observation target irradiated with illumination light and excitation light simultaneously, the image being formed of reflection light of the illumination light reflected from the observation target and fluorescence emitted from the observation target excited by the excitation light;

calculating, with respect to each pixel of the obtained image signal, estimated spectroscopic data in a particular fluorescence wavelength range which is a wavelength range that includes at least a substantial center wavelength of the fluorescence from an image signal of each pixel and estimated matrix data stored in advance for calculating estimated spectroscopic data, obtaining a quasi fluorescence image signal that includes an image signal attributable to the fluorescence based on the estimated spectroscopic data in the particular fluorescence wavelength range, and generating a quasi ordinary image signal by subtracting the quasi fluorescence image signal from the obtained image signal.

Another image obtaining apparatus of the present invention is an apparatus, including:

a light emitting unit for emitting illumination light and excitation light onto an observation target simultaneously;

an imaging unit for obtaining an image formed of reflection light of the illumination light reflected from the observation target and fluorescence emitted from the observation target irradiated with the excitation light;

a first storage unit for storing estimated matrix data for calculating estimated spectroscopic data;

an estimated spectroscopic data calculation unit for calculating, with respect to each pixel of the image signal outputted from the imaging unit, estimated spectroscopic data in a particular fluorescence wavelength range which is a wavelength range including at least a substantial center wavelength of the fluorescence using an image signal of each pixel and the estimated matrix data; and an image processing unit having a quasi fluorescence image signal generation unit for generating a quasi fluorescence image signal that includes an image signal attributable to the fluorescence based on the estimated spectroscopic data in the particular fluorescence wavelength range calculated by the estimated spectroscopic data calculation unit, and a quasi ordinary image signal generation unit for generating a quasi ordinary image signal by subtracting the quasi fluorescence image signal from the image signal obtained by the imaging unit.

The term "estimated matrix data for calculating estimated spectroscopic data" as used herein refers to matrix data taken into account the spectroscopic property of light such as the illumination light or the like and the spectroscopic property of the imaging unit and allow estimated spectroscopic data that includes estimated spectral reflectivity information of the observation target to be calculated by performing a matrix operation with an image signal. The team "a particular fluorescence wavelength range which is a wavelength range that includes at least a substantial center wavelength of the fluorescence" as used herein refers to a wavelength range that includes at least the center wavelength of the fluorescence or a wavelength adjacent to the center wavelength, which may be a wavelength range in which an intensity of the fluorescence is substantially reflected.

If the image processing unit has a fluorescence emission intensity information calculation unit for obtaining fluorescence emission intensity information, which is information reflecting an emission intensity of the fluorescence emitted from the observation target, from the estimated spectroscopic data in the particular fluorescence wavelength range, and the apparatus further includes a second storage unit for storing, in advance, a relationship between fluorescence emission intensity information of fluorescence emitted from a plurality of observation samples and fluorescence image signals obtained by imaging the fluorescence emitted from the plurality of observation samples by the imaging unit, the plurality of observation samples having a fluorescence property substantially identical to that of the observation target and emitting fluorescence of different emission intensities when irradiated with the excitation light, then the quasi fluorescence image signal generation unit may be a unit that generates the quasi fluorescence image signal based on the fluorescence emission intensity information obtained by the fluorescence emission intensity information calculation unit and the relationship stored in the second storage unit.

If the light emitting unit is a unit that emits reference light having a wavelength range different from that of the excitation light onto the observation target simultaneously with the emission of the excitation light and the imaging unit is a unit that obtains an image that includes reflection light of the reference light reflected from the observation target, then the fluorescence emission intensity information calculation unit may be a unit that calculates a reference light intensity, which is an intensity of the reflection light of the reference light obtained by the imaging unit, calculates a pseudo fluorescence intensity, which is a light intensity in the particular fluorescence wavelength range from the estimated spectroscopic data in the particular fluorescence wavelength range, and calculates a pseudo fluorescence yield obtained by diving the pseudo fluorescence intensity by the reference light intensity as the fluorescence emission intensity information.

The apparatus may further include an input unit for setting the particular fluorescence wavelength range by an input operation.

The first storage unit and second storage unit may be those provided separately or a single storage unit that performs both functions.

According to the image obtaining method and apparatus, illumination light and auxiliary light having a wavelength range different from that of the illumination light are emitted onto an observation target to which, for example, a medical agent that absorbs light having the wavelength of the auxiliary light is administered to obtain an image formed of reflection light of the illumination light and reflection light of the auxiliary light reflected from the observation target, then estimated spectroscopic data in the wavelength range of the auxiliary light is calculated with respect to each pixel of the obtained image signal using a value of the image signal and estimated matrix data in the wavelength range of the auxiliary light stored in advance, quasi reflectivity information reflecting a reflectivity of the observation target in the wavelength range of the auxiliary light is obtained based on the estimated spectroscopic data in the wavelength range of the auxiliary light, and a special image is generated based on the quasi reflectivity information. The simultaneous emission of the illumination light and auxiliary light may prevent the reduction in the number of frames per unit time of the special image based on reflection light of the auxiliary light, whereby a favorable display image may be obtained even when the special image is displayed, for example, as a moving picture. Further, the emission of illumination light and the emission of auxiliary light need not be switched so that the structure of light emitting unit may be simplified.

According to another image obtaining method and apparatus, from an observation target irradiated with illumination light and excitation light simultaneously, an image formed of reflection light of the illumination light reflected from the observation target and fluorescence emitted from the observation target excited by the excitation light is obtained, then, with respect to each pixel of the obtained image signal, estimated spectroscopic data in a particular fluorescence wavelength range which is a wavelength range that includes at least a substantial center wavelength of the fluorescence is calculated from an image signal of each pixel and estimated matrix data stored in advance for calculating estimated spectroscopic data, a quasi fluorescence image signal that includes an image signal attributable to the fluorescence is obtained based on the estimated spectroscopic data in the particular fluorescence wavelength range, and a quasi ordinary image signal is generated by subtracting the quasi fluorescence image signal from the obtained image signal. By subtracting the quasi fluorescence image signal from the obtained image signal, i.e. from raw data, a quasi ordinary image signal having a low content rate of image signal attributable to the fluorescence may be generated. Then, a quasi ordinary image generated from the quasi ordinary image signal may be used as the substitute of an ordinary image obtained by emitting only illumination light, whereby the user-friendliness is enhanced. Further, the number of frames of the quasi ordinary image which may be obtained per unit time is not reduced, so that even when the quasi ordinary image is displayed as a moving picture, a favorable image may be provided.

BRIEF DESCRIPTION OF THE DRAWINGS

FIG. 21 illustrates a lookup table.

FIG. 22 illustrates spectra of fluorescence emitted from a normal tissue and a diseased tissue.

DESCRIPTION OF THE PREFERRED EMBODIMENTS

Hereinafter, embodiments of the present invention will be described in detail. First, an image obtaining apparatus (first embodiment) in which illumination light and auxiliary light are emitted onto an observation target simultaneously to obtain an image formed of refection light of the illumination light and reflection light of the auxiliary light reflected from the observation target, and a special image reflecting a medical agent distribution in the observation target is generated from an image signal of the image will be described. Thereafter, an image obtaining apparatus (fluorescence image obtaining apparatus, second and third embodiments) in which illumination light and excitation light are emitted onto an observation target simultaneously to obtain an image formed of refection light of the illumination light reflected from the observation target and fluorescence emitted from the observation target, and a fluorescence image reflecting a fluorescence emission intensity is generated from an image signal of the image will be described.

Figure 1:
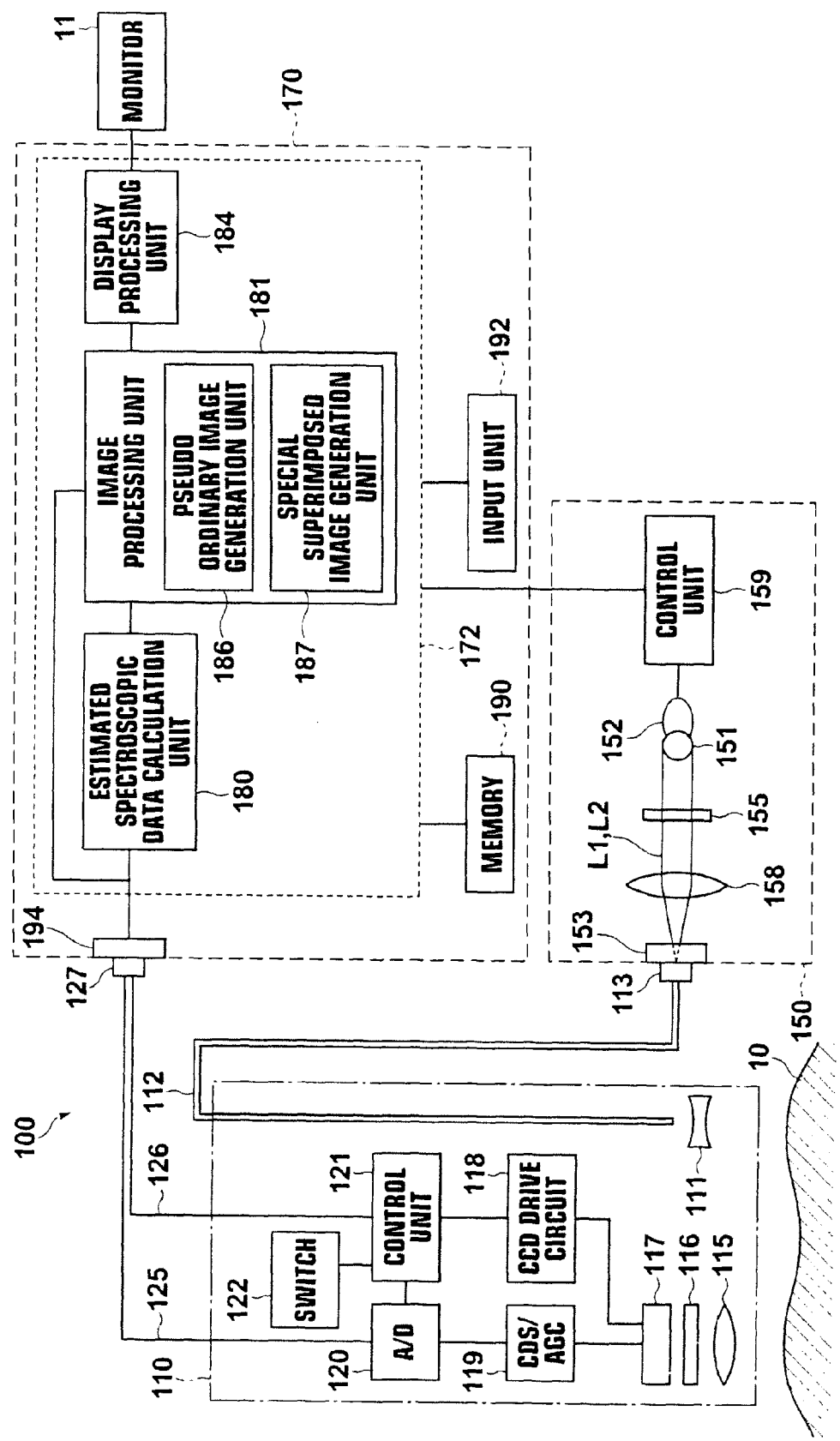
FIG. 1 is a block diagram of an endoscope system according to a first embodiment of the present invention, illustrating the configuration thereof.

FIG. 1 illustrates a schematic configuration of an endoscope system according to a first embodiment to which an image obtaining apparatus of the present invention is applied. Endoscope system 100 is a system that emits visible illumination light L1 and auxiliary light L2 with a center wavelength of 805 nm onto observation target 10 administered with ICG (indocyanine green) having light absorbing property at a wavelength of 805 nm in advance to obtain an image signal, generates a pseudo ordinary image and a special superimposed image superimposed with a special image reflecting the reflectivity information of the observation target at a wavelength of 805 nm, and displays each of the images as a moving picture.

As shown in FIG. 1, endoscope system 100 includes scope unit 110 to be inserted into a body cavity of a subject and used to observe observation target 10, processor unit 170 to which scope unit 110 is removably attached and electrically connected, and light source unit 150 to which scope unit 110 is removably attached and optically connected and having therein xenon lamp 151 that emits illumination light L1 and auxiliary light L2. Note that processor unit 170 and light source unit 150 may be formed integrally or separately.

Illumination optical system 111 is provided at a distal end portion of scope unit 110. One end of light guide 112 to which illumination light L1 and auxiliary light L2 are guided is positioned opposite to illumination optical system 111. Light guide 112 is configured to extend outside scope unit 110 and optical connector 113 is provided to the other end thereof, which is removably connected to optical connector 153 of light source unit 150, to be described later.

Further, imaging lens 115 and CCD (charge coupled device) 117, which is a solid-state image sensor, are concentrically provided in this order at the distal end portion of scope unit 110. Imaging lens 115 forms an image of observation target 10 on CCD 117. For example, primary three-color filter 116 having RGB color filters is attached to the image forming surface of CCD 117. CCD 117 is connected to CCD drive circuit 118 that generates a drive pulse based on a synchronization signal and CDS/AGC (correlated double sampling/automatic gain control) circuit 119 that samples and amplifies an image (video) signal outputted from CCD 117. CDS/AGC circuit 119 is connected to A/D converter 120 that digitizes the analog output of CDS/AGC circuit 119. Further, control unit 121 is provided inside of scope unit 110 that controls various circuits provided therein and also controls communication with processor unit 170. Depression switch 122 connected to control unit 121 and used for switching operation modes is provided at a proximal end portion of scope unit 110. One end of signal line 125 is connected to A/D converter 120 and one end of signal line 126 is connected to control unit 121.

Signal line 125 and signal line 126 extend from the body of scope unit 110 to the outside and connector 127 is provided at the other end of each signal line. Connector 127 is removably connected to connector 194 of processor unit 170, to be described later.

Light source unit 150 includes xenon lamp 151, drive circuit 152 for driving xenon lamp 151, and optical connector 153, removably connected to optical connector 113, provided at the tip of light guide 112 of scope unit 110. Wavelength filter 155 and condenser lens 158 are provided between xenon lamp 151 and optical connector 153. Further, control unit 159 for controlling drive circuit 152 is provided in light source unit 150.

Figure 2:
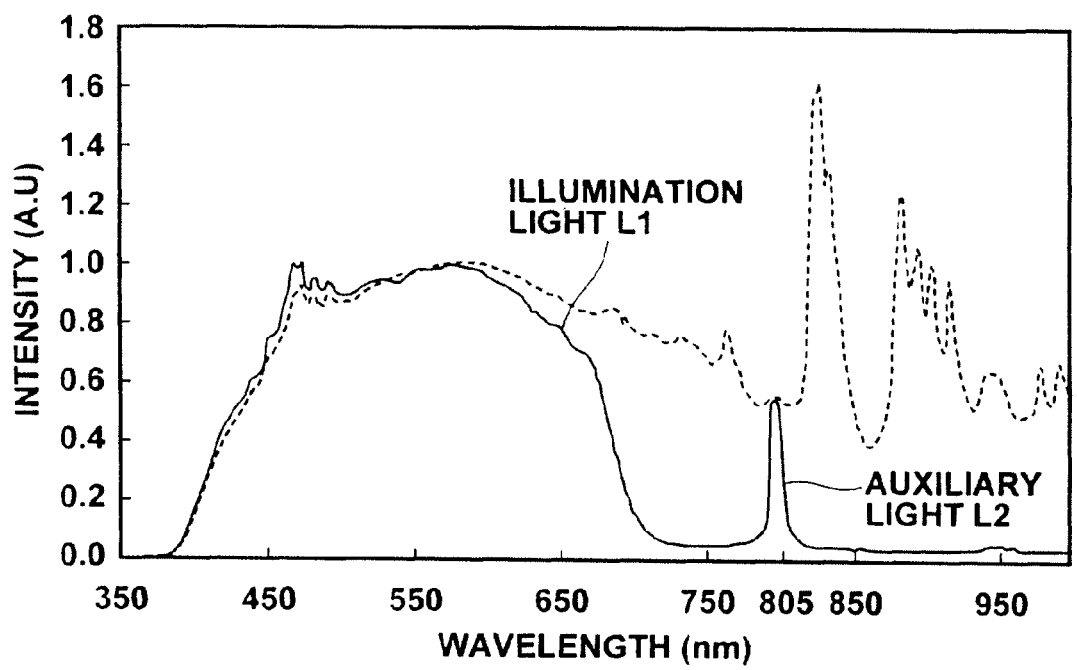
FIG. 2 illustrates spectra of illumination light and auxiliary light.

FIG. 2 illustrates spectrum of light emitted from xenon lamp 151 and spectra of illumination light L1 and auxiliary light L2. In FIG. 2, the dotted line represents the spectrum of the light emitted from xenon lamp 151 and the solid line represents the spectra of illumination light L1 and auxiliary light L2.

Wavelength filter 155 transmits light in the wavelength range from 400 to 700 nm and light with a wavelength of 805 nm. Accordingly, the light emitted from xenon lamp 151 turns to illumination light L1 in the wavelength range from 400 to 700 nm and auxiliary light with a wavelength of 805 nm after passed through the wavelength filter 155.

Processor unit 170 includes processor 172 that performs various types of signal processing and control. Processor 172 includes estimated spectroscopic data calculation unit 180, image processing unit 181, and display processing unit 184. Memory 190, keyboard type input unit 192, and connector 194 removably connected to connector 127 of scope unit 110 are connected to processor 172. Further, control unit 121 of scope unit 110 and control unit 159 of light source unit 150 are connected to processor 172.

Estimated spectroscopic data calculation unit 180 calculates, with respect to each pixel, estimated spectroscopic data in the wavelength range of auxiliary light using R, G, B three color image signal outputted from A/D converter 120 of scope unit 110 and estimated matrix data in the wavelength range of 805 nm of auxiliary light stored in memory 190 in advance, and outputs the data to image processing unit 181. Likewise, estimated spectroscopic data calculation unit 180 calculates estimated spectroscopic data in the wavelength of 700 nm using R, G, B three color image signal outputted from A/D converter 120 of scope unit 110 and estimated matrix data in the wavelength of 700 nm stored in memory 190 in advance, and outputs the data to image processing unit 181.

Image processing unit 181 includes pseudo ordinary image generation unit 186 for generating pseudo ordinary image data and special superimposed image generation unit 187 for generating special superimposed image data. Operations of pseudo ordinary image generation unit 186 and special superimposed image generation unit 187 will be described in detail later.

Display processing unit 184 generates a normal display color image signal in which pseudo ordinary image data and special superimposed image data are arranged side by side and outputs the signal to monitor 11.

Memory 190 has estimated matrix data for calculating estimated spectroscopic data of observation target 10. The estimated matrix data are stored in memory 190 in advance as a table. The estimated matrix data are matrix data taken into account the spectroscopic property of the light emitted onto observation target 10, i.e. illumination light L1 and auxiliary light L2, and the spectroscopic property of the entire imaging system including the color sensitivity characteristic of the image sensor, transmission factors of the color filters, and the like. Calculation between RGB image signal obtained by CCD 117 and the estimated matrix data allows acquisition of spectroscopic data of observation target 10 which do not depend on the spectroscopic properties of illumination light and auxiliary light, intrinsic spectroscopic property of the imaging system, and the like. The detail of the estimated matrix data is disclosed, for example, in Japanese Unexamined Patent Publication No. 2003-093336 and U.S. Patent Application Publication No. 20070183162. An example of estimated matrix data stored in memory 190 in the present embodiment is shown in Table 1 below.

TABLE 1

| PARAMETER | $k_{pr}$ | $k_{pg}$ | $k_{pb}$ |
|---|---|---|---|
| p1 | $k_{1r}$ | $k_{1g}$ | $k_{1b}$ |
| . | . | . | . |
| . | . | . | . |
| . | . | . | . |

TABLE 1-continued

| PARAMETER | $k_{pr}$ | $k_{pg}$ | $k_{pb}$ |
|---|---|---|---|
| p18 | $k_{18r}$ | $k_{18g}$ | $k_{18b}$ |
| p19 | $k_{19r}$ | $k_{19g}$ | $k_{19b}$ |
| p20 | $k_{20r}$ | $k_{20g}$ | $k_{20b}$ |
| p21 | $k_{21r}$ | $k_{21g}$ | $k_{21b}$ |
| p22 | $k_{22r}$ | $k_{22g}$ | $k_{22b}$ |
| p23 | $k_{23r}$ | $k_{23g}$ | $k_{23b}$ |
| . | . | . | . |
| . | . | . | . |
| p43 | $k_{43r}$ | $k_{43g}$ | $k_{43b}$ |
| p44 | $k_{44r}$ | $k_{44g}$ | $k_{44b}$ |
| p45 | $k_{45r}$ | $k_{45g}$ | $k_{45b}$ |
| p46 | $k_{46r}$ | $k_{46g}$ | $k_{46b}$ |
| p47 | $k_{47r}$ | $k_{47g}$ | $k_{47b}$ |
| p48 | $k_{48r}$ | $k_{48g}$ | $k_{48b}$ |
| p49 | $k_{49r}$ | $k_{49g}$ | $k_{49b}$ |
| p50 | $k_{50r}$ | $k_{50g}$ | $k_{50b}$ |
| . | . | . | . |
| . | . | . | . |
| p60 | $k_{60r}$ | $k_{60g}$ | $k_{60b}$ |
| p61 | $k_{61r}$ | $k_{61g}$ | $k_{61b}$ |
| p82 | $k_{82r}$ | $k_{82g}$ | $k_{82b}$ |

The matrix data shown in Table 1 includes 61 wavelength range parameters (coefficient sets) p1 to p61 provided, for example, by dividing wavelength range from 400 to 700 nm by an interval of 5 nm and wavelength range parameter p82 corresponding to the wavelength of 805 nm. In the present embodiment, light in the wavelength range from 705 to 800 nm is not emitted to observation target 10 so that wavelength range parameters (coefficient sets) p62 to p81 are omitted.

For example, estimated spectroscopic data (q1 to q61, q82) may be generated by performing a matrix operation represented by the formula below on an R, G, B three color image signal using the matrix of 3×62, i.e. all of the parameters of estimated matrix data stored in memory 190.

$$\begin{bmatrix} q_1 \\ q_2 \\ \vdots \\ q_{61} \\ q_{82} \end{bmatrix} = \begin{bmatrix} k_{1r} & k_{1g} & k_{1b} \\ k_{2r} & k_{2g} & k_{2b} \\ \vdots & \vdots & \vdots \\ k_{61r} & k_{61g} & k_{61b} \\ k_{82r} & k_{82g} & k_{82b} \end{bmatrix} \times \begin{bmatrix} R \\ G \\ B \end{bmatrix}$$

Figure 3:
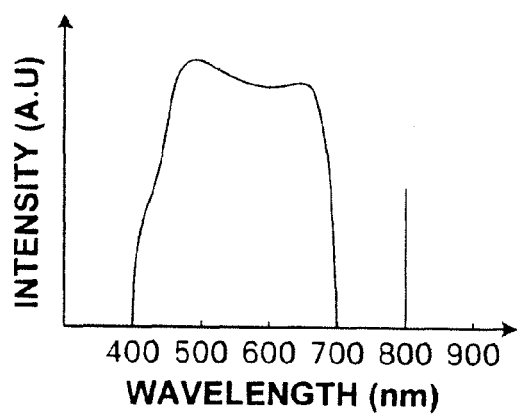
FIG. 3 illustrates estimated spectroscopic data as a spectral distribution.
Figure 4:
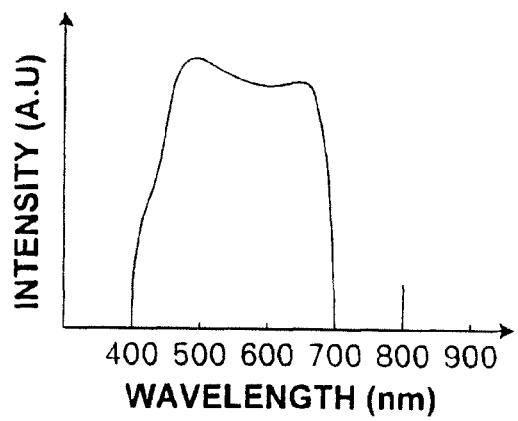
FIG. 4 illustrates estimated spectroscopic data as a spectral distribution.

FIGS. 3 and 4 illustrate examples of estimated spectroscopic data (q1 to q61, q82) as spectral distributions. FIG. 3 illustrates estimated spectroscopic data in a pixel corresponding to an area of observation target 10 where ICG is not present, i.e. estimated spectroscopic data when 805 nm auxiliary light L2 is not absorbed by ICG.

FIG. 4 illustrates estimated spectroscopic data in a pixel corresponding to an area of observation target 10 where ICG is present, i.e. estimated spectroscopic data when 805 nm auxiliary light L2 is absorbed by ICG. In each graph, horizontal axis represents the wavelength corresponding to each data value q1 to q61, q82 and horizontal axis represents the intensity of each data value q1 to q61, q82.

In an area where ICG is not present, a significant amount of 805 nm auxiliary light L2 is reflected, as shown in FIG. 3, while in an area where ICG is present, 805 nm auxiliary light L2 is absorbed by ICG and virtually not reflected. That is, the estimated spectroscopic data value (q82) at 805 nm is a value reflecting the reflectivity of 805 nm auxiliary light L2 at observation target 10, and at the same time, a value reflecting the absorption or non-absorption of auxiliary light L2 by ICG.

In the present embodiment, a special image is generated based on the estimated spectroscopic data value (q82) at 805 nm.

Correspondence table T representing the relationship between the light intensity at 805 nm and RGB signal obtained by measurement is also stored in memory 190 in advance.

An operation of the endoscope system of the present embodiment structured in the manner as described above will now be described. Preceding the operation of the endoscope system, cleaned and disinfected scope unit 110 is attach to processor unit 170 and light source unit 150. Connector 127 provided at the tip of each of signal lines 125 and 126 of scope unit 110 is connected to connector 194 of processor unit 170. Optical connector 113 provided at the tip of light guide 112 is connected to optical connector 153 of light source unit 150.

Thereafter, scope unit 110 is inserted in a body cavity, e.g. esophagus, of a subject to obtain an image of observation target 10. ICG is administered to the subject, for example, by an intravenous injection at a predetermined time before or during the image acquisition of observation target 10. The administered ICG is carried by blood current of the subject to observation target 10.

When a predetermined key of input unit 192 or switch 122 of scope unit 110 is depressed by the user, xenon lamp 151 of light source unit 150 is turned on by drive circuit 152. Light emitted from xenon lamp 151 is passed through wavelength filter 155 and limited in the wavelength range, thereby turning into illumination light L1 in the wavelength range from 400 to 700 nm and auxiliary light L2 with a wavelength of 805 nm, which are condensed on the end face of optical connector 113 by condenser lens 158 and inputted to light guide 112. Illumination light L1 and auxiliary light L2 propagated through light guide 112 exit from the tip of light guide 112 and emitted onto observation target 10 through illumination optical system 111.

CCD 117 driven by CCD drive circuit 118 obtains an image of observation target 10 and outputs the imaged signal. The imaged signal is subjected to the correlated double sampling and amplification by automatic gain control in CDS/AGC circuit 119, which is then A/D converted by A/D converter 120 and inputted to estimated spectroscopic data calculation unit 180 and image processing unit 181 of processor 172 of processor unit 170 as RGB image signal.

Estimated spectroscopic data calculation unit 180 calculates, with respect to each pixel, an estimated spectroscopic data value (q82) at 805 nm by performing a matrix operation represented by the formula shown below using R, G, B three color image signal outputted from A/D converter 120 of scope unit 110 and estimated matrix data in the wavelength range of 805 nm of auxiliary light stored in memory 190 in advance, and outputs the data value to pseudo ordinary image generation unit 186 and special superimposed image generation unit 187 of image processing unit 181.

$$q_{82} = [k_{82r}, k_{82g}, k_{82b}] \times \begin{bmatrix} R \\ G \\ B \end{bmatrix}$$

Likewise, estimated spectroscopic data calculation unit 180 calculates, with respect to each pixel, an estimated spectroscopic data value (q61) at 700 nm by performing a matrix operation represented by the formula shown below using R, G, B three color image signal outputted from A/D converter 120 of scope unit 110 and estimated matrix data in the wavelength range of 700 nm stored in memory 190 in advance, and outputs the data value to special superimposed image generation unit 187 of image processing unit 181.

$$q_{61} = [k_{61r}, k_{61g}, k_{61b}] \times \begin{bmatrix} R \\ G \\ B \end{bmatrix}$$

Pseudo ordinary image generation unit 186 calculates, with respect to each pixel, RGB image signal attributable to auxiliary light L2 based on the estimated spectroscopic data value (q82) and correspondence table T between the light intensity at 805 nm and RGB signals stored in memory 190, and generates a special image (auxiliary light image) formed of these image signals.

In the mean time, the image formed of R, G, B three color image signal outputted from A/D converter 120 of scope unit 110 is a mixed image of an ordinary image formed of reflection light of illumination light L1 and an image formed of reflection light of auxiliary light L2 superimposed on top of each other, and the auxiliary light image can be regarded as the image formed of reflection light of auxiliary light 12.

Pseudo ordinary image generation unit 186 subtracts, with respect to each pixel, RGB image signal at 805 nm from RGB image signal outputted from A/D converter 120 of scope unit 110, i.e. subtracts the auxiliary image from the mixed image to generate a pseudo ordinary image which can be virtually regarded as a normal image and outputs the pseudo ordinary image to display processing unit 184.

Next, a special superimposed image generation procedure performed in special superimposed image generation unit 187 will be described with reference to the flowchart shown in FIG. 5.

In step S101, light intensity ratio r is calculated with respect to each pixel by dividing the estimated spectroscopic data value (q82) by the estimated spectroscopic data value (q61).

The intensity of auxiliary light L2 reflected at observation target 10, i.e. reflection light of auxiliary light L2 is substantially proportional to the luminance of auxiliary light L2 but the illuminance of auxiliary light L2 decreases in inversely proportional to the square of the distance. Consequently, there may be a case in which reflection light stronger than that of an area where ICG is not present located remote from the light source is received from an area where ICG is present located near the light source. Thus, it is impossible to know whether or not ICG is present in the area only with the information of reflection light intensity of auxiliary light. Consequently, a method for generating an image is known in which light having a wavelength range different from that of the auxiliary light is emitted onto an observation target as reference light, then the intensity of reflection light of reference light (reference light intensity) reflected by the observation target is detected, a light intensity ratio is obtained by dividing the reflection light intensity of the auxiliary light by the reference light intensity, and an image is generated based on the light intensity ratio. The light intensity ratio reduces the influence of difference in distance from the tip of scope unit 110 to each region of observation target 10 or the influence of variation in emission intensity of auxiliary light L2. The light intensity ratio is a value reflecting a reflectivity of light in the wavelength range of auxiliary light at each region of an observation target, and corresponds to quasi reflectivity information.

In the present embodiment, the estimated spectroscopic data value at 805 nm (q82) is used as the reflection light intensity of the auxiliary light described above, and the estimated spectroscopic data value at 700 nm (q61) is used as the reference light intensity. The wavelength of 700 nm is a wavelength at which the absorbance by oxygenated hemoglobin is minimal in the wavelength range of illumination light L1, and hence is a wavelength insusceptible to the existence or nonexistence of a blood vessel. If the estimated spectroscopic data value at 700 nm (q61) is 0, the light intensity ratio diverges. Therefore, when calculating the light intensity ratio, it is preferable to check to see that the estimated spectroscopic data value at 700 nm (q61) is not 0 first, then to calculate the ratio.

As the reference light, light having a wavelength in the red to infrared region and equally penetrates into a tissue with auxiliary light L2 is preferably used. For example, a red component of illumination light L1 may be used. Alternatively, for example, near infrared light having any desired wavelength in the range from 700 to 1000 nm (excluding a region around 805 nm) may be used. The reference light component may be removed by the processing identical to that of auxiliary light L2 when generating a pseudo ordinary image.

In step S102, light intensity ratio r is compared to predetermined upper and lower limit values in order to reduce the influence of noise when the signal intensity is low, in which light intensity ratio r greater than the upper limit value is set to the upper limit value and light intensity ratio r lower than the lower limit value is set to the lower limit value. Note that a value of 0 may be set to light intensity ratio r greater than the upper limit value and light intensity ratio r lower than the lower limit value as invalid.

Figure 6:
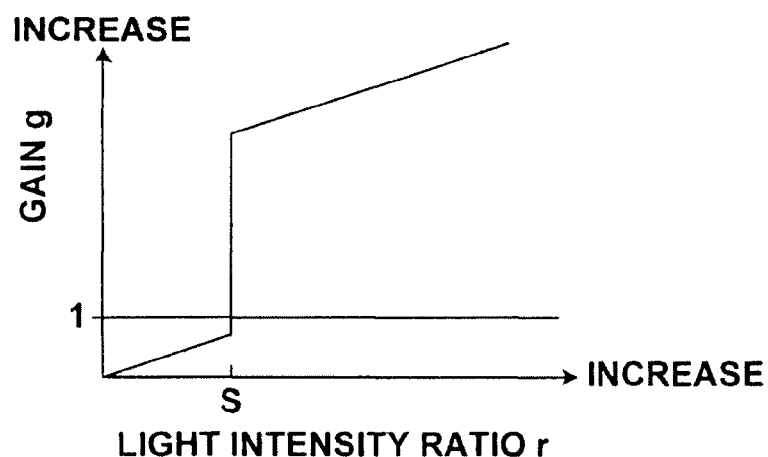
FIG. 6 illustrates a gain setting method.

In step S103, with respect to each pixel, the light intensity ratio is compared to reference value S stored in memory 190 in advance, and if the light intensity ratio is smaller than reference value S, gain g smaller than 1 is set, while if the light intensity ratio is greater than reference value S, gain g greater than 1 is set, as shown in FIG. 6.

In step S104, with respect to each pixel, the estimated spectroscopic data value at 805 nm (q82) is multiplied by gain g calculated in step S103 to generate enhanced light intensity signal m=the estimated spectroscopic data value (q82)·g.

In step S105, with respect to each pixel, RGB image signal corresponding to enhanced light intensity signal m is calculated using the enhanced light intensity signal m calculated in step S104 and correspondence table T between the light intensity at 805 nm and RGB signal stored in memory 190. The image formed of RGB image signal corresponding to enhanced light intensity signal m corresponds to a special image generated based on quasi reflectivity information reflecting the reflectivity of light in the wavelength range of the auxiliary light of the present invention at each region of an observation target.

In step S106, with respect to each pixel, RGB image signal corresponding to enhanced light intensity signal m calculated in step S105 is added to RGB image signal outputted from A/D converter 120 of scope unit 110. That is, a special superimposed image is generated by superimposing a special image formed of RGB signal generated in step S105 on a mixed image formed of RGB signal outputted from A/D converter 120 of scope unit 110 and the special superimposed image is outputted to display processing unit 184.

Display processing unit 184 generates a display image in which the pseudo ordinary image and special superimposed image are arranged side by side, and outputs the display image to monitor 11 for display. In the special superimposed image, an area having a large light intensity ratio, i.e. an area where ICG is not present, is displayed brightly because the light intensity is increased, and an area where ICG is present is displayed relatively dark, so that the visibility of the ICG presence area is improved.

As clear from the description above, a pseudo ordinary image and a special superimposed image can be obtained at the same time. Therefore, when, for example, displaying the pseudo ordinary image and special superimposed image as a moving picture, the number of frames per second is not reduced and favorable display images may be obtained. Further, the emission of illumination light L1 and the emission of auxiliary light L2 need not be switched so that the structure of light source unit 150 may be simplified.

Figure 7A:
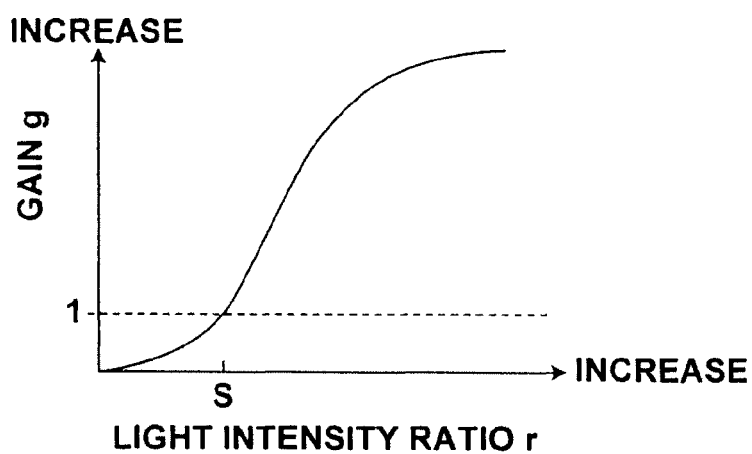
FIG. 7A illustrates a gain setting method.
Figure 7B:
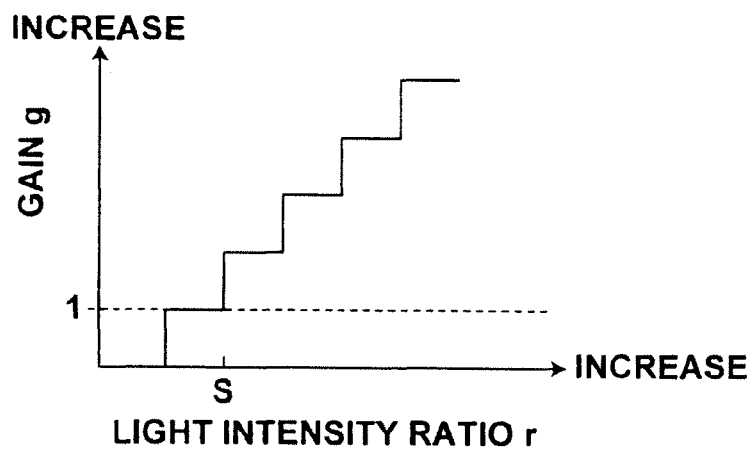
FIG. 7B illustrates a gain setting method.

In the present embodiment if light intensity ratio r is smaller than reference value S, gain g smaller than 1 is set, while if light intensity ratio r is greater than reference value S, gain g greater than 1 is set in step S103, as shown in FIG. 6. The gain may be set in various different ways. For example, the gain may be set in a continuous manner as shown in FIG. 7A, or in a stepwise manner as shown in FIG. 7B.

Figure 5:
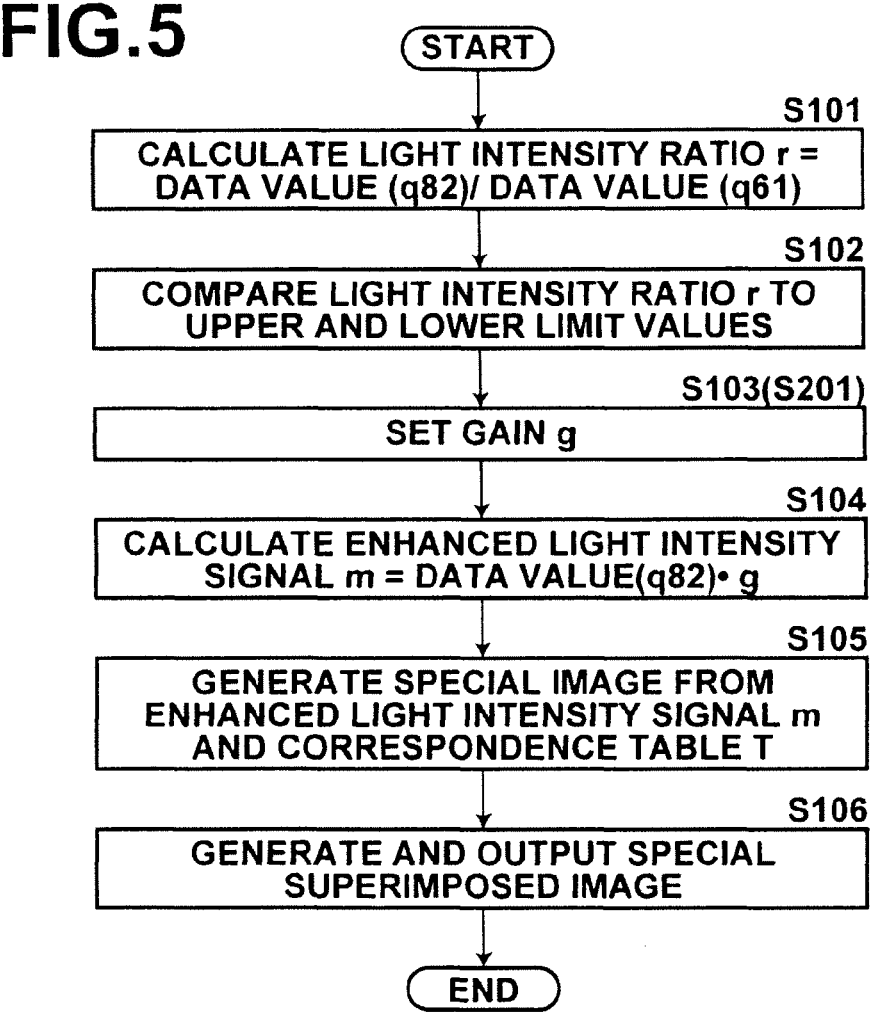
FIG. 5 illustrates a special superimposed image generation procedure.
Figure 8:
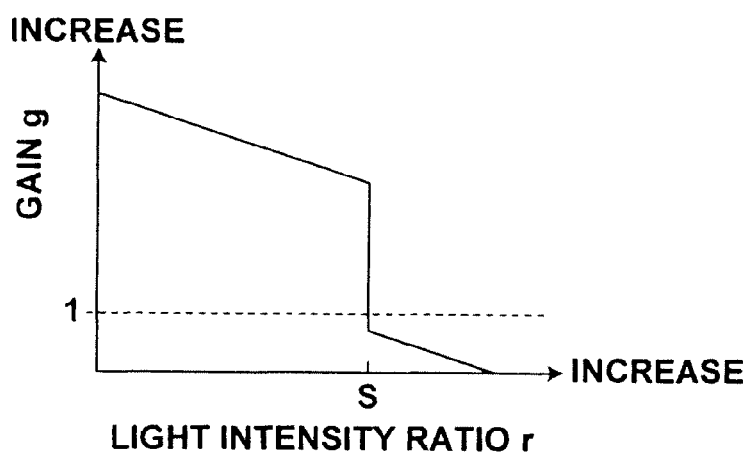
FIG. 8 illustrates a gain setting method.
Figure 9:
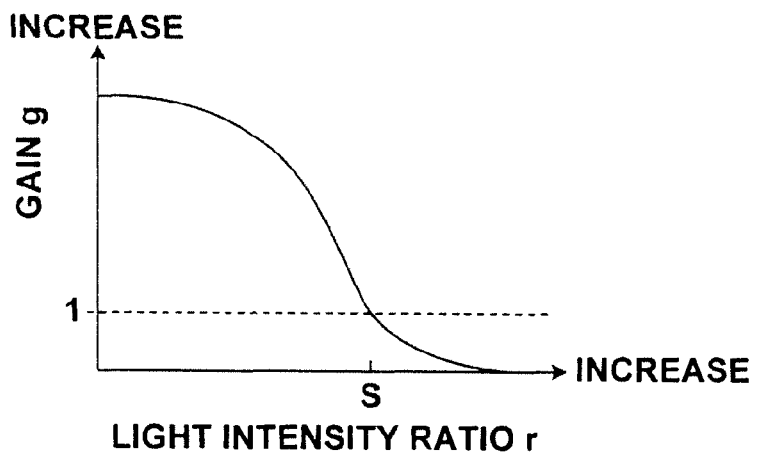
FIG. 9 illustrates a gain setting method.

Alternatively, as shown in FIG. 5, step S201 may be performed instead of step S103. In step S201, light intensity ratio r is smaller than reference value S, gain g greater than 1 is set, while if light intensity ratio r is greater than reference value S, gain g smaller than 1 is set, as shown in FIG. 8. Further, in step S201, as shown in FIG. 9, the gain may be set in a continuous manner. In this case, an area having a small light intensity ratio, i.e. an area where ICG is present is displayed brightly, whereby the visibility of the ICG presence area is improved.

Figure 10:
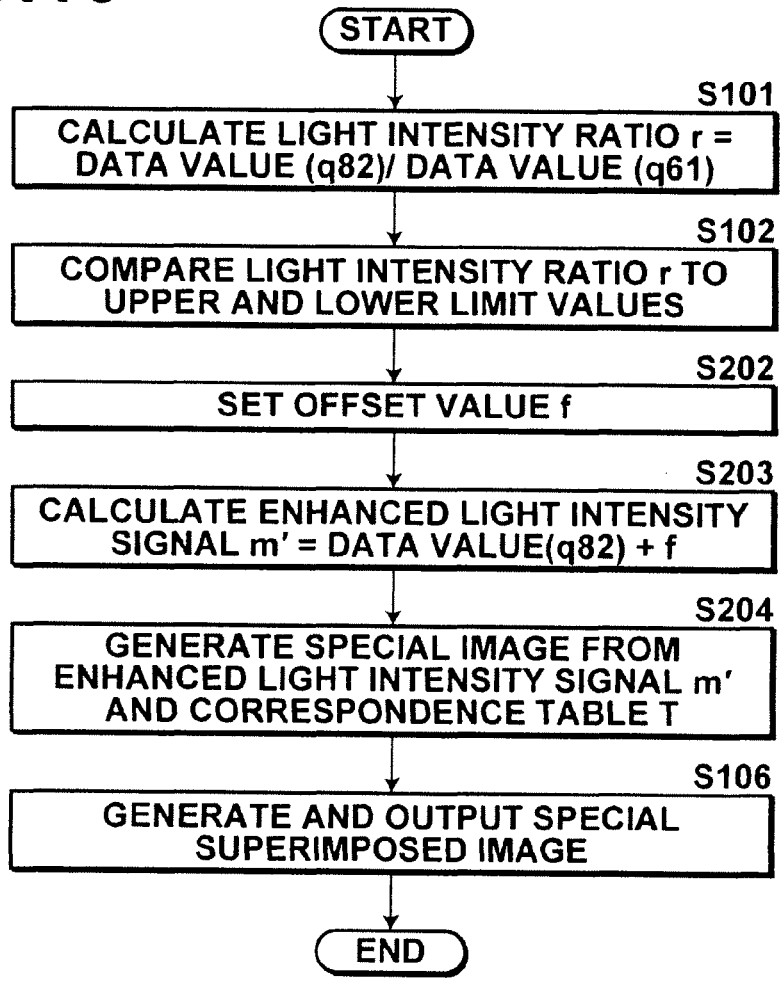
FIG. 10 illustrates a special superimposed image generation procedure.
Figure 11:
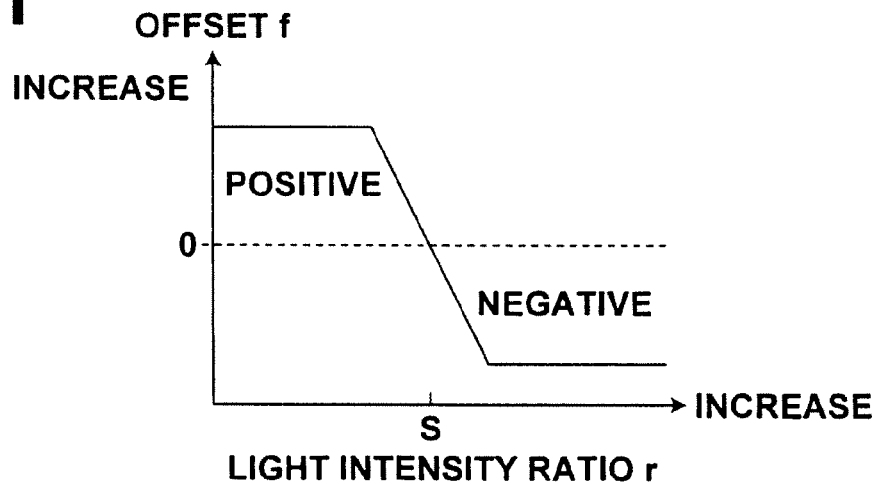
FIG. 11 illustrates an offset setting method.

Further, as shown in FIG. 10, steps S202 to S204 may be performed instead of steps S103 to S105. In step S202, if light intensity ratio r is smaller than reference value S, positive offset value f greater than 1 is set, while if light intensity ratio r is greater than reference value S, negative offset value f greater than 1 is set as shown in FIG. 11. In step S203, with respect to each pixel, offset value f calculated in step S202 is added to estimated spectroscopic data value at 805 nm (q82) to generate enhanced light intensity signal m'=estimated spectroscopic data value at 805 nm (q82)+offset value f. In step S204, with respect to each pixel, RGB image signals corresponding to enhanced light intensity signal m' are calculated using the enhanced light intensity signal m' calculated in step S203 and correspondence table T between the light intensity at 805 nm and RGB signals stored in memory 190, thereby generating a special image. In this case also, an area having small light intensity ratio r, i.e. ICG presence area is displayed brightly, whereby the visibility of the ICG presence area is improved.

Figure 12:
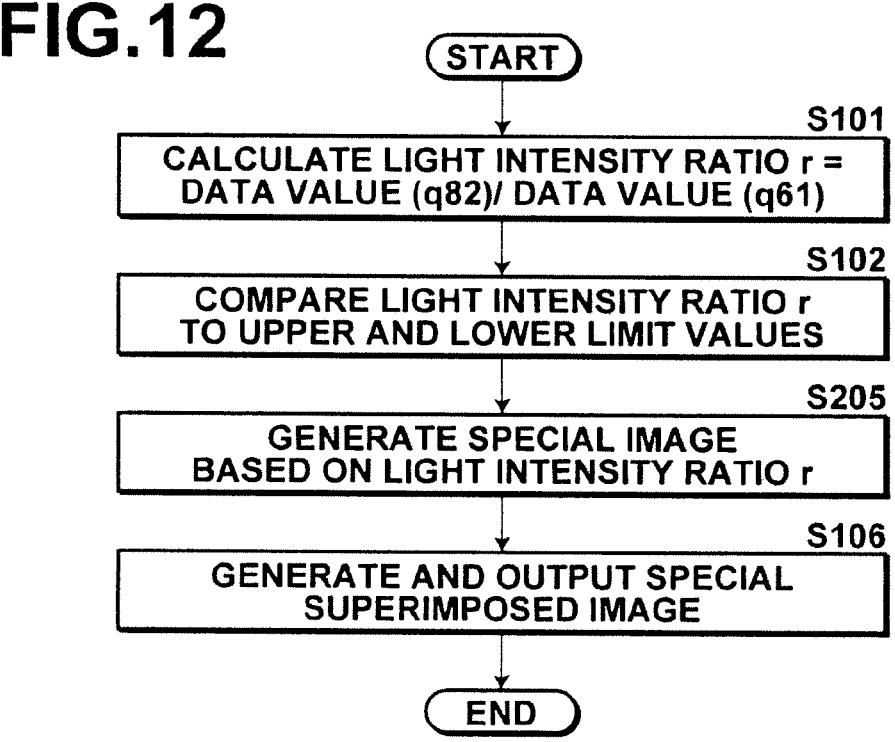
FIG. 12 illustrates a special superimposed image generation procedure.

Still further, as shown in FIG. 12, step S205 may be performed instead of steps S103 to S105. In step S205, if light intensity ratio r is smaller than reference value S, a saturated value is set as an RGB signal, while if light intensity ratio r is greater than reference value S, value of 0 is set as RGB signal to generate a special image. In this case, an area where ICG is present shines white and the other area is displayed as an ordinary color image. For example, when detecting a sentinel lymph node which is a lymph node to which a lymph stream reaches first, the lymph node where ICG is present shines white, so that the sentinel lymph node can be detected easily.

In the present embodiment, the description of the image obtaining apparatus of the present invention has been described using an endoscope system in which illumination light L1 and auxiliary light L2 emitted from light source unit 150 and propagated through scope unit 110 are emitted onto observation target 10 simultaneously and an image is generated through CCD 117. But, the embodiment of the image obtaining apparatus of the present invention is not limited to that described above. That is, the invention may take any form as long as it obtains an image by emitting illumination light and auxiliary light onto an observation target simultaneously. The light source of the auxiliary light may be an LED. The invention is applicable, for example, to an endoscope system having a light source unit of LED or the like at the tip of scope unit 110, colposcope, capsule endoscope system, or the like. Otherwise, it may be a microscope having image acquisition capabilities or the like.

Further, primary three-color filter 116 is described as the mosaic filter of CCD 117, but the type of filter is not limited to this, and a four color mosaic filter, complementary mosaic filter, or the like may also be used. In such a case, a signal outputted from CCD 117 may be converted to a primary color signal by signal processing or estimated matrix data based on the spectroscopic properties of these mosaic filters may be stored in a memory in advance.

Next, a fluorescence image obtaining apparatus will be described.

Figure 13:
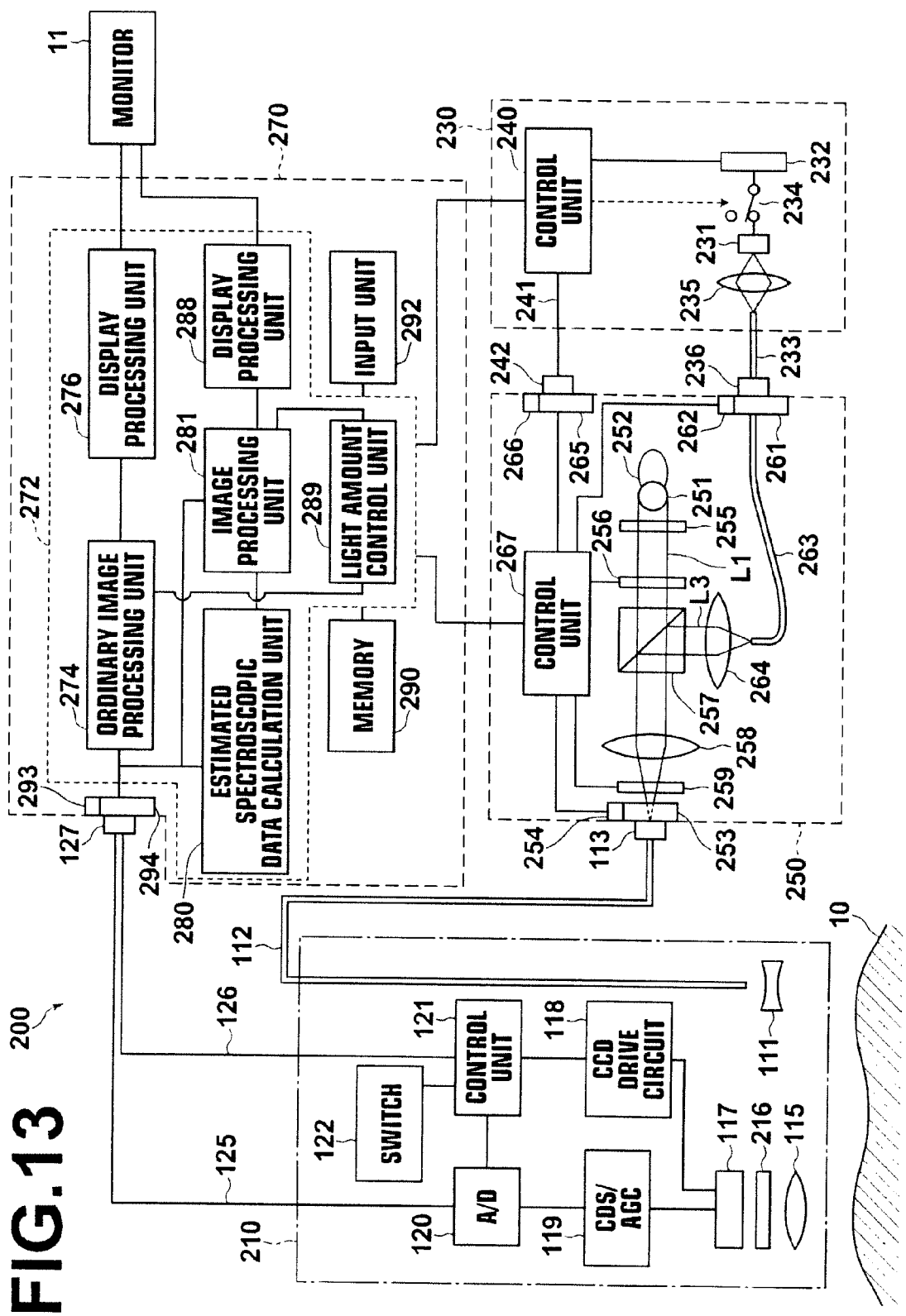
FIG. 13 is a block diagram of a fluorescence endoscope system according to a second embodiment of the present invention, illustrating the configuration thereof.

FIG. 13 illustrates a schematic configuration of an endoscope system (fluorescence endoscope system) according to a second embodiment to which a fluorescence image obtaining apparatus of the present invention is applied. Fluorescence endoscope system 200 is a system that operates in an ordinary image mode in which an ordinary image represented by three colors (color ordinary image) obtained by emitting illumination light L1 onto observation target 10 is displayed as a moving picture, or in a fluorescence image mode in which a quasi color ordinary image and a fluorescence image which can be obtained from a color ordinary image obtained by emitting illumination light L1 and excitation light L3 onto observation target 10 by arithmetic processing, to be described later, are displayed as a moving picture.

As shown in FIG. 13, fluorescence endoscope system 200 includes scope unit 210 to be inserted into a body cavity of a subject and used to observe observation target 10, processor unit 270 to which scope unit 210 is removably attached and electrically connected, illumination light unit 250 to which scope unit 210 is removably attached and optically connected and having therein xenon lamp 251 that emits illumination light L1, and excitation light unit 230 removably attached and electrically and optically connected to illumination light unit 250 and having therein GaN system semiconductor laser 231 that emits excitation light L3. Note that processor unit 270 and illumination light unit 250 may be formed integrally or separately. Elements identical to those of the first embodiment will not be elaborated upon further here unless otherwise specifically required.

Scope unit 210 is identical to that described earlier, and optical connector 253 of illumination light unit 250, to be described later, is removably connected to optical connector 113. Further, connector 294 of processor unit 270, to be described later, is removably connected to connector 127. Control unit 121 is connected so as to perform communication control with processor unit 270. Excitation light cut filter 216 is disposed on the imaging surface of CCD 117. For example, a primary color filter having RGB color filters may also be attached to the imaging surface of CCD 117.

Illumination light unit 250 includes xenon lamp 251 for emitting illumination light L1, drive circuit 252 for driving xenon lamp 251, and connector 253, removably connected to optical connector 113, provided at the tip of light guide 112 of scope unit 210. Optical connector 253 includes connection detector 254 for detecting whether or not optical connector 253 is connected to optical connector 113. Wavelength filter 255 that limits the wavelength range of illumination light L1 from 410 to 700 nm, aperture 256 that controls the amount of illumination light L1, dichroic mirror 257 that transmits light having a wavelength not smaller than 410 nm and orthogonally reflects light having a wavelength shorter than 410 nm, condenser lens 258, and rotary shutter 259 are disposed between xenon lamp 251 and optical connector 253. Illumination light unit 250 further includes optical connector 261 removably connected to optical connector 236 provided at the tip of light guide 233 of excitation light unit 230, to be described later. Optical connector 261 includes connection detector 262 for detecting whether or not optical connector 261 is connected to optical connector 236. One end (input end) of light guide 263 that guides excitation light within illumination light unit 250 is connected to optical connector 261. The other end (output end) of light guide 263 is placed at a position where excitation light L3 outputted from light guide 263 is inputted to dichroic mirror 257. Further, collimator lens 264 is disposed between the output end of light guide 263 and dichroic mirror 257.

Illumination light unit 250 further includes connector 265 removably connected to connector 242 of excitation light unit 230 to be described later. Connector 265 includes connection detector 266 for detecting whether or not connector 265 is connected to connector 242. Illumination light unit 250 further includes control unit 267, connected to each element in illumination light unit 250, such as connection detector 266 or the like, for controlling each element and performing communication control with processor unit 270 and excitation light unit 230.

Excitation light unit 230 includes GaN system semiconductor laser 231 that emits excitation light L3, drive circuit 232 for driving semiconductor laser 231, and light guide 233 for guiding excitation light L3 emitted from semiconductor laser 231. Light guide 233 extends from the housing of excitation light unit 230 to the outside, and optical connector 236 is provided at the other end thereof. Optical connector 236 is removably connected to optical connector 261 of illumination light unit 250. Switch 234 is provided between semiconductor laser 231 and drive circuit 232. Condenser optical system 235 is disposed between semiconductor laser 231 and one end (input end) of light guide 233.

Excitation light unit 230 further includes control unit 240, connected to each element in excitation light unit 230, such as drive circuit 232, switch 234, or the like, for controlling each element and performing communication control with illumination light unit 250. One end of signal line 241 is connected to control unit 240. Signal line 241 extends from the housing of excitation light unit 230 to the outside and connector 242 is provided at the other end thereof. Connector 242 is removably connected to connector 265 of illumination light unit 250.

Processor unit 270 includes processor 272. Processor 272 includes ordinary image processing unit 274 and display processing unit 276 that perform signal processing when the ordinary image mode is selected, estimated spectroscopic data calculation unit 280, image processing unit 281, and display processing unit 288 when the fluorescence image mode is selected, and light amount control unit 289.

When the ordinary image mode is selected, ordinary image processing unit 274 performs various types of signal processing on R, G, B three color image signal outputted from A/D converter 120 of scope unit 210, then generates a Y/C signal constituted by a luminance (Y) signal and chrominance [C (R-Y, B-Y)] signals, and outputs the Y/C signal to display processing unit 276. Display processing unit 276 performs various types of signal processing on the Y/C signal to generate a display color ordinary image signal and outputs the color ordinary image signal to monitor 11 of, for example, liquid crystal display device, CRT, or the like.

When the fluorescence image mode is selected, estimated spectroscopic data calculation unit 280 obtains, with respect to each pixel, estimated spectroscopic data in a particular fluorescence wavelength range, which is a wavelength range including a center wavelength range of 490 nm of fluorescence emitted from observation target 10 when irradiated with excitation light L3, e.g. from 470 to 510 nm, using R, G, B three color image signal outputted from A/D converter 120 of scope unit 210 and estimated matrix data stored in memory 290 in advance for calculating spectroscopic data and outputs the estimated spectroscopic data to image processing unit 281.

Figure 14:
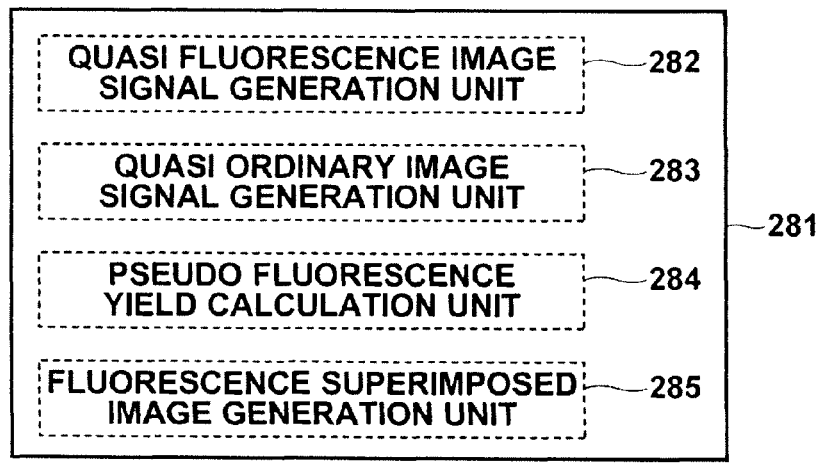
FIG. 14 is a block diagram of the image processing unit, illustrating the configuration thereof.

As shown in FIG. 14, image processing unit 281 includes quasi fluorescence image signal generation unit 282 and quasi ordinary image signal generation unit 283 for generating a quasi ordinary image, and pseudo fluorescence yield calculation unit 284 and fluorescence superimposed image generation unit 285 for generating a fluorescence superimposed image. Quasi fluorescence image signal generation unit 282, quasi ordinary image signal generation unit 283, pseudo fluorescence yield calculation unit 284, and fluorescence superimposed image generation unit 285 will be described in detail later.

Light amount control unit 289, when connected to ordinary image processing unit 274 and image processing unit 281 and illumination ordinary image mode is selected, controls the light amount of illumination light L1 based on the luminance of a color ordinary image. Further, when fluorescence image mode is selected, light amount control unit 289 controls the light amounts of illumination light L1 and excitation light L3 based on the luminance of a pseudo color ordinary image.

Memory 290, keyboard type input unit 292, and connector 294 removably connected to connector 127 of scope unit 210 are connected to processor 272. Connector 294 includes connection detector 293 for detecting whether or not connector 294 is connected to connector 127. Further, processor 272 is connected to control unit 121 of scope unit 210, control unit 267 of illumination light unit 250, and control unit 240 of excitation light unit 230.

Memory 290 has estimated matrix data for calculating estimated spectroscopic data of observation target 10, as in the first embodiment. The estimated matrix data are stored in memory 290 in advance as a table. The estimated matrix data of the present embodiment are 59 wavelength parameters (coefficient sets) p1 to p59 divided, for example, the wavelength range from 410 to 700 nm by an interval of 5 nm (Table 1).

An operation of the endoscope system 200 of the present embodiment structured in the manner as described above will now be described. First, an operation of the endoscope system in the ordinary image mode in which a color ordinary image obtained by emitting illumination light L1 onto observation target 10 is displayed as a moving picture will be described.

Preceding the operation of the endoscope system, cleaned and disinfected scope unit 210 is attached to processor unit 270 and light source unit 250. Connector 127 provided at the tip of each of signal lines 125 and 126 of scope unit 210 is connected to connector 294 of processor unit 270. Optical connector 113 provided at the tip of light guide 112 is connected to optical connector 253 of light source unit 250. When connector 127 is connected to connector 294, connection detector 293 of connector 294 outputs a connection signal to processor 272. Further, when optical connector 113 is connected to optical connector 253, connection detector 254 of connector 253 outputs a connection signal to control unit 267.

When connection signals are inputted from connection detectors 293 and 254, processor 272 rotates rotary shutter 259 of illumination light unit 250 to enable the operation in the ordinary image mode, sets a functional configuration of a predefined key of input unit 292, and sets the functional configuration of switch 122 via control unit 121 of scope unit 210. When the user depresses the predefined key of input unit 292 or switch 122, the operation mode is switched between halt condition and ordinary image mode through control of processor 272.

When the predetermined key of input unit 292 or switch 122 is depressed once by the user, the operation in the ordinary image mode is started. In illumination light unit 250, xenon lamp 251 is turned on by drive circuit 252 and illumination light L1 is emitted. Illumination light L1 is condensed on the end face of optical connector 113 through wavelength filter 255, aperture 256, and dichroic mirror 257 and inputted to light guide 112. Illumination light L1 propagated through light guide 112 is outputted from the tip of light guide 112 and emitted onto observation target 10 through illumination optical system 111.

The wavelength range of illumination light L1 is limited in the range from 410 to 700 nm by wavelength filter 255. The light amount control of illumination light L1 by aperture 256 will be described later.

CCD 117 driven by CCD drive circuit 118 takes an image of observation target 10 and outputs an imaged signal. The imaged signal is subjected to the correlated double sampling and amplification by automatic gain control in CDS/AGC circuit 119, which is then A/D converted by A/D converter 120 and inputted to ordinary image processing unit 274 of processor 272 of processor unit 270 as RGB image signal. When the ordinary image mode is selected, ordinary image processing unit 274 performs various types of image processing on R, G, B three color images outputted from A/D converter of scope unit 210, generates a Y/C signal (color ordinary image signal) constituted by luminance signal Y and chromatic chrominance signals C, and outputs the Y/C signal to display processing unit 276. Display processing unit 276 performs various types of signal processing, including I/P conversion and noise reduction, on the Y/C signal and outputs the processed signal to monitor 11.

Further, ordinary image processing unit 274 outputs luminance signal Y of each pixel or average luminance signal Y' of a plurality of adjacent pixels to light amount control unit 289. Light amount control unit 289 calculates average luminance value Ya of pixels in an specified area with respect to each frame, compares the calculated value to reference luminance value Yr stored in memory 290 in advance, selects an aperture control signal based on a result of the comparison, and outputs the selected signal to control unit 267 of illumination light unit 250. As the aperture control signal, a signal for decreasing the aperture value of aperture 256 is selected when average luminance value Ya is greater than reference luminance value Yr, a signal for increasing the aperture value of aperture 256 is selected when average luminance value Ya is smaller than reference luminance value Yr, and a signal for maintaining the current aperture value is selected when average luminance value Ya substantially corresponds to reference luminance value Yr.

Control unit 267 of illumination light unit 250 controls the aperture value of aperture 256 based on the aperture control signal.

Next, an operation of the endoscope system in the fluorescence image mode will be described. Before the start of the fluorescence image mode, cleaned and disinfected scope unit 210 is attached to processor unit 270 and light source unit 250. The attachment method and output of connection signals are identical to those in the ordinary image mode described above.

In addition, excitation light unit 230 is connected to illumination light unit 250. Connector 242 at the tip of signal line 241 of excitation light unit 230 is connected to connector 265 of illumination light unit 250. When connector 242 is connected to connector 265, connection detector 266 of connector 265 outputs a connection signal to control unit 267. In addition, optical connector 236 at the tip of light guide 233 is connected to optical connector 261 of illumination light unit 250. When optical connector 236 is connected to optical connector 261, connection detector 262 of connector 261 outputs a connection signal to control unit 267.

Control unit 240 of excitation light unit 230 communicates with control unit 267 of illumination light unit 250 and, when connection signals are inputted from connection detectors 266 and 262, closes switch 234 of excitation light unit 230 to electrically connect semiconductor laser 231 to drive circuit 232, allowing drive circuit 232 to drive semiconductor laser 231. Further, control unit 240 sets a functional configuration of a predefined key of input unit 292 via processor 272 of processor unit 270, and sets a functional configuration of switch 122 via processor 272 and control unit 121 of scope unit 210. When the user depresses the predefined key of input unit 292 or switch 122, the operation mode is switched between halt condition and ordinary image mode through control of control unit 240. When the connection signal is inputted from neither of connection detectors 266 and 262, or when the connection signal is not inputted from either one of connection detectors 266 and 262, switch 234 in excitation light unit 230 is open. Thus, semiconductor laser 231 is never driven when excitation light unit 230 is not connected to illumination light unit 250.

When the endoscope system is operated in the ordinary image mode, a predetermined key of input unit 292 or switch 122 is depressed once by the user, the operation in the fluorescence image mode is started.

In addition to illumination light unit 250, excitation light unit 230 starts operation. Semiconductor laser 231 is driven by drive circuit 232 and excitation light L3 having a wavelength of 405 nm is emitted. Excitation light L3 is condensed by condenser optical system 235 and incident on the end face of light guide 233. Excitation light L3 propagated through light guide 233 is inputted to light guide 263 through optical connectors 236 and 261. Excitation light L3 propagated through light guide 263 and outputted from the tip thereof is converted to parallel light by collimator lens 264 and inputted to dichroic mirror 257. Excitation light L3, having a wavelength of 405 nm, is orthogonally reflected by dichroic mirror 257, condensed on the end face of optical connector 113 by collimator lens 258, and inputted to light guide 112. Excitation light propagated through light guide 112 is outputted from the tip thereof and emitted onto observation target 10 through illumination optical system 111. Here, note that illumination light L1 is also emitted onto observation target 10 at the same time. The amount of excitation light L3 is controlled by the drive current of drive circuit 232. The light amount control by the drive current will be described later.

CCD 117 driven by CCD drive circuit 118 takes an image formed of reflection light of illumination light L1 reflected from observation target 10 and fluorescence emitted from observation target 10 irradiated with excitation light L3. Excitation light cut filter 216 for cutting off light having a wavelength not greater than 410 nm is provided at the front of CCD 117, and therefore reflection light of excitation light L3 is not substantially incident on CCD 117. CCD 117 outputs an imaged signal. The imaged signal is subjected to the correlated double sampling and amplification by automatic gain control in CDS/AGC circuit 119, which is then A/D converted by A/D converter 120 and inputted to estimated spectroscopic data calculation unit 280 and image processing unit 281 of processor 272 of processor unit 270 as RGB image signals.

Using a matrix of 3×9 of parameters (p13 to p21) of estimated matrix data stored in memory 290 corresponding to a particular fluorescence wavelength range, which is a wavelength range including a center wavelength of 490 nm of fluorescence emitted from observation target 10 when irradiated with excitation light L3, e.g. a particular fluorescence wavelength range from 470 to 510 nm, estimated spectroscopic data calculation unit 280 generates, with respect to each pixel, estimated spectroscopic data (q13 to q21) by performing a matrix operation represented by the formula below on R, G, B three color image signal and outputs the data to image processing unit 281.

$$\begin{bmatrix} q_{13} \\ q_{14} \\ \vdots \\ q_{21} \end{bmatrix} = \begin{bmatrix} k_{13r} & k_{13g} & k_{13b} \\ k_{14r} & k_{14g} & k_{14b} \\ & \vdots & \\ k_{21r} & k_{21g} & k_{21b} \end{bmatrix} \times \begin{bmatrix} R \\ G \\ B \end{bmatrix}$$

Figure 15A:
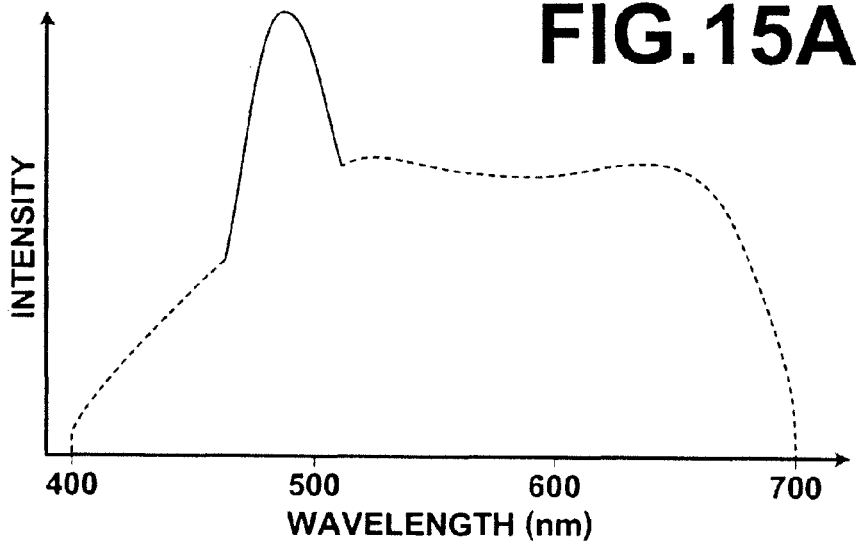
FIG. 15A illustrates the relationship between wavelength and estimated spectroscopic data.
Figure 15B:
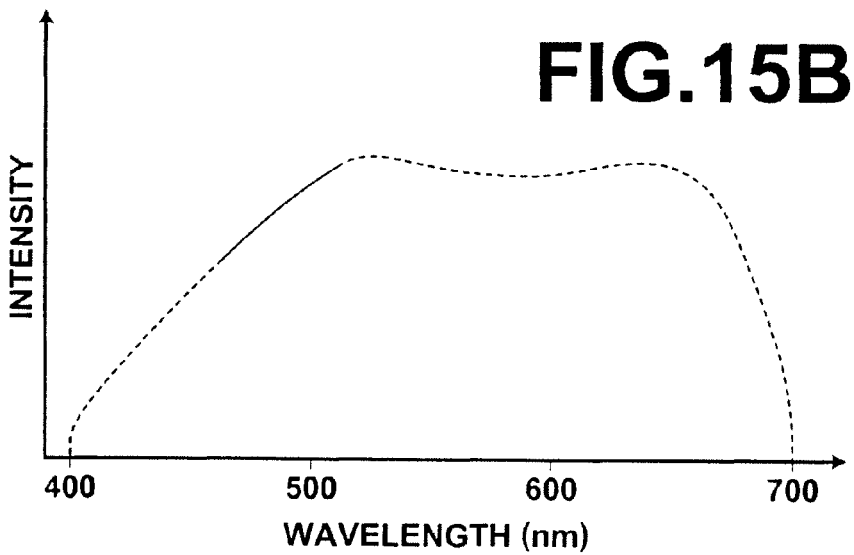
FIG. 15B illustrates the relationship between wavelength and estimated spectroscopic data.

FIGS. 15A and 15B illustrate examples of spectral distributions of estimated spectroscopic data (q13 to q21) generated with respect to each pixel. The solid line portion represents a spectral distribution of the obtained estimated spectroscopic data (q13 to q21), and the dotted line portion represents estimated spectroscopic data of other wavelength ranges (410 to 465 nm and 515 to 700 nm) for reference. FIG. 15A illustrates a spectral distribution of a pixel corresponding to observation target 10 from which fluorescence is emitted, and FIG. 15B illustrates a spectral distribution of a pixel corresponding to observation target 10 from which fluorescence is not emitted. In each of the graphs, the horizontal axis represents the wavelength corresponding to each of data values q13 to q21 of the estimated spectroscopic data and the vertical axis represents the intensity of each of data values q13 to q21.

As shown in FIG. 15B, the spectral distribution obtained from observation target 10 from which fluorescence is not emitted is a distribution reflecting the spectral reflectivity of observation target 10. More specifically, the intensity of each of data values q13 to q21 becomes a value reflecting the product of the spectral reflectivity of observation target 10 and the intensity of light incident on each pixel of CCD 117.

As shown in FIG. 15A, the spectral distribution of estimated spectroscopic data (q13 to q21) obtained from observation target 10 from which fluorescence is emitted is a distribution reflecting the spectral reflectivity of observation target 10 and the spectral emissivity of the fluorescence adjacent to the wavelength of 490 nm, i.e. the center wavelength of the fluorescence. More specifically, the intensity of each of data values q1 to q59 becomes a value reflecting the spectral reflectivity of observation target 10, spectral emissivity of emitted fluorescence, and intensity of light incident on each pixel of CCD 117. The estimated matrix data used for providing estimated spectroscopic data (q13 to q21) are matrix data for estimating the spectral reflectivity of observation target 10. Thus, each of data values q13 to q21 is not a value accurately reflecting the spectral emissivity of the fluorescence but includes infatuation on whether the spectral emissivity is large or small. Therefore, quasi color ordinary image and fluorescence superimposed image can be generated using spectroscopic data (q13 to q21) of a particular fluorescence wavelength range, as will be described hereinafter.

Image processing unit 281 performs the following signal processing with respect to each pixel. A method for generating a quasi color ordinary image signal will be described first. From the estimated spectroscopic data (q13 to q21) in the particular fluorescence wavelength range (470 to 510 nm), quasi fluorescence image signal generation unit 282 of image processing unit 281 obtains three color image signal (Rs, Gs, Bs) in the particular fluorescence wavelength range and outputs the signals to quasi ordinary image signal generation unit 283. For example, where wavelength range of B (blue) is 410 to 500, that of G (green) is 505 to 600 nm, and that of R (red) is 605 to 700 nm, image signal Bs can be obtained by adding from spectroscopic data values q13 (470 nm) to q19 together, and image signal Gs can be obtained by adding spectroscopic data values q20 (505 nm) and q21 (510 nm). Image signal Rs is set to 0, since the corresponding spectroscopic data value is not present. In the present embodiment, image signal Rs is set to 0, since the particular fluorescence wavelength range does not include R (red) wavelength range, but where the particular fluorescence wavelength range includes R (red) wavelength range, image signal Rs is calculated in the similar manner as described above.

Quasi ordinary image generation unit 283 subtracts the three color image signal (Rs, Gs, Bs) from the three color image signal (R, G, B) inputted from scope unit 210 to generate a three color image signal (R-Rs, G-Gs, B-Bs) of quasi color ordinary image, generates a Y/C signal constituted by a luminance signal Y and chrominance signals C (quasi color ordinary image signal) from the three color image signal (R-Rs, G-Gs, B-Bs) of quasi color ordinary image and outputs the Y/C signal to display processing unit 288. When generating the Y/C signal, it is preferable that a correction considering the size of each wavelength range is performed, in addition to various types of signal processing. Display processing unit 288 combines the quasi color ordinary image and fluorescence superimposed image, to be described later, into a single image and displays the image on monitor 11.

Next, a method for generating a fluorescence superimposed image signal will be described. Pseudo fluorescence yield calculation unit 284 adds up each of estimated spectroscopic data q13 to q21 in the particular fluorescence wavelength range (470 to 510 nm) to calculate pseudo fluorescence intensity D.

Intensity (emission intensity) of fluorescence emitted from a phosphor is substantially proportional to the illuminance of excitation light, but the illuminance of excitation light decreases in inversely proportional to the square of the distance. Consequently, there may be a case in which stronger fluorescence is received from a diseased tissue located close to the light source than that from a normal tissue located remote from the light source. Thus, accurate determine of tissue characteristic of the observation target can not be made only with fluorescence intensity information. Consequently, it has been practiced to emit light having a wavelength range different from that of the excitation light onto an observation target as reference light, detect the intensity of reflection light of the reference light reflected from the observation target (reference light intensity E), obtain a fluorescence yield by dividing the fluorescence intensity by the reference light intensity E as fluorescence emission intensity information, and generate a fluorescence image based on the fluorescence yield.

Figure 16:
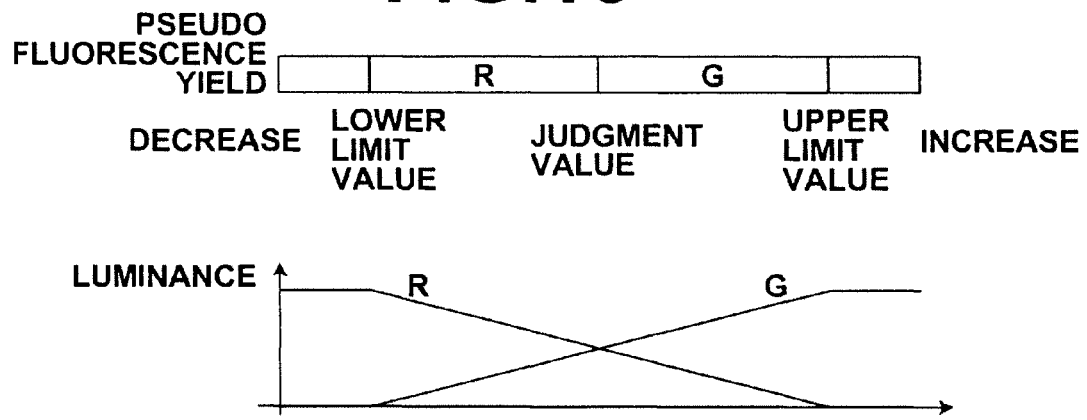
FIG. 16 illustrates the relationship between pseudo fluorescence yield and display color.

Pseudo fluorescence yield calculation unit 284 of image processing unit 281 obtains pseudo fluorescence yield F using the value of luminance signal Y of the quasi color ordinary image signal described above as reference light intensity E, i.e. by dividing pseudo fluorescence intensity D by the value of luminance signal Y of the quasi color ordinary image signal and outputs obtained pseudo fluorescence yield F to fluorescence superimposed image generation unit 285. Fluorescence superimposed image generation unit 285, for example, allocates green to pseudo fluorescence yield F if it is greater than a predetermined judgment value or allocates red if it is smaller than the predetermined judgment value as shown in FIG. 16, thereby generating a fluorescence image. Alternatively, a fluorescence image in which display color sequentially changes to red, yellow, and green according to the value of pseudo fluorescence yield F by mixing red and green by the additive color mixing method. When the value of pseudo fluorescence yield F is not greater than a predetermined lower limit value, only red may be allocated, and when the value of pseudo fluorescence yield F is not smaller than a predetermined upper limit value, only green may be allocated, in which case, a diseased tissue with a small pseudo fluorescence yield F is displayed in red, while a normal tissue with a large pseudo fluorescence yield F is displayed in green.

Figure 17:
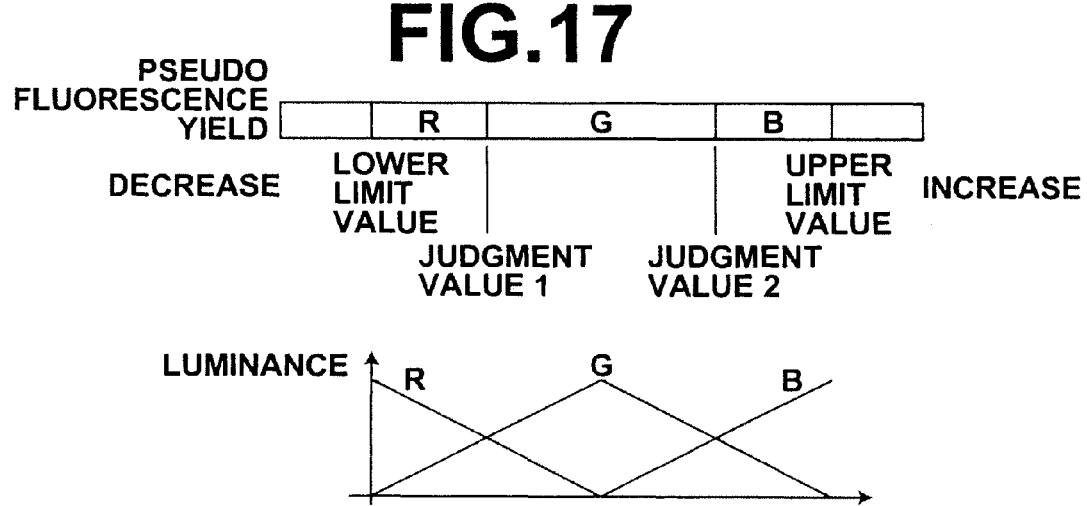
FIG. 17 illustrates the relationship between pseudo fluorescence yield and display color.

Otherwise, a fluorescence image may also be generated by allocating red, green, or blue to the pseudo fluorescence yield F through a comparison with a judgment value, as shown in FIG. 17. Further, a fluorescence image in which display color sequentially changes to red, yellow, green, cyan, and blue according to the value of pseudo fluorescence yield F by mixing red, green, and blue by the additive color mixing method. When the value of pseudo fluorescence yield F is not greater than a predetermined lower limit value or not smaller than a predetermined upper limit value, achromatic color may be allocated.

In the present embodiment, the value of luminance signal Y of a quasi color ordinary image signal is used as the reference light intensity. But, instead of the value of luminance signal Y of a quasi color ordinary image signal, for example, the light intensity of image signal Rs or the light intensity obtained from estimated spectroscopic data in a long wavelength range in which the difference in intensity between fluorescence emitted from a normal tissue and fluorescence emitted from a diseased tissue is small, e.g. at 620 nm, may be used.

Fluorescence superimposed image generation unit 285 of image processing unit 281 generates fluorescence superimposed image data in which the fluorescence image is superimposed on an image reflecting only luminance signal Y of quasi color ordinary image signal, i.e., a quasi achromatic ordinary image so that the user may easily recognize the position of a diseased tissue in which pseudo fluorescence yield F becomes small and outputs the fluorescence superimposed image data to display processing unit 288.

Display processing unit 288 generates a display image signal, in which quasi color ordinary image data and fluorescence superimposed image data outputted from image processing unit 281 are displayed side by side, or a display color ordinary image signal in which quasi color ordinary image data and fluorescence superimposed image data are combined into a single image, and outputs the image signal to monitor 11 for display.

Note that an arrangement may be adopted in which a determination is made by processor 272 in advance as to whether or not pseudo fluorescence yield F of each pixel is greater than a predetermined judgment value, and if all of the values are greater than the predetermined value, i.e., when there is not any area corresponding to a diseased tissue in the image, only the quasi color ordinary image data are displayed.

Further, image processing unit 281 outputs luminance signal Y of the quasi color ordinary image signal of each pixel or average luminance signal Y' of a plurality of adjacent pixels to light amount control unit 289. Light amount control unit 289 calculates average luminance value Ya of pixels in a specified area with respect to each frame, compares the calculated value to reference luminance value Yr stored in memory 290 in advance, selects an aperture control signal based on a result of the comparison, and outputs the selected signal to control unit 267 of illumination light unit 250. At the same time, a drive current control signal for controlling the value of drive current supplied from drive circuit 232 to semiconductor laser 231 in excitation light unit 230 is obtained and outputted to control unit 240 of excitation light unit 230.

As the aperture control signal, a signal for decreasing the aperture value of aperture 256 is selected when average luminance value Ya is greater than reference luminance value Yr, a signal for increasing the aperture value of aperture 256 is selected when average luminance value Ya is smaller than reference luminance value Yr, and a signal for maintaining the current aperture value is selected when average luminance value Ya substantially corresponds to reference luminance value Yr. Further, a drive current control signal corresponding to the aperture control signal is outputted so that the ratio between the amount of illumination light L1 and amount of excitation light L3 becomes a predetermined value. The ratio between the amount of illumination light L1 and amount of excitation light L3 can be set in advance through an input operation from input unit 292, and light amount control unit 289 determines the amount of drive current of semiconductor laser 231 based on the ratio set in advance and the aperture value for illumination light L1 and outputs a drive current control signal.

Control unit 267 of illumination light unit 250 controls the aperture value of aperture 256 based on the aperture control signal. Further, control unit 240 of excitation light unit 230 controls the current value supplied from drive circuit 232 to semiconductor laser 231 based on the drive current control signal.

As clear from the description above, in fluorescence endoscope system 200 according to the present invention, the pseudo color ordinary image and fluorescence superimposed image may have the same number of frames per unit time as that of the color ordinary image. This allows a favorable display image to be generated even when it is displayed as a moving picture.

Figure 18:
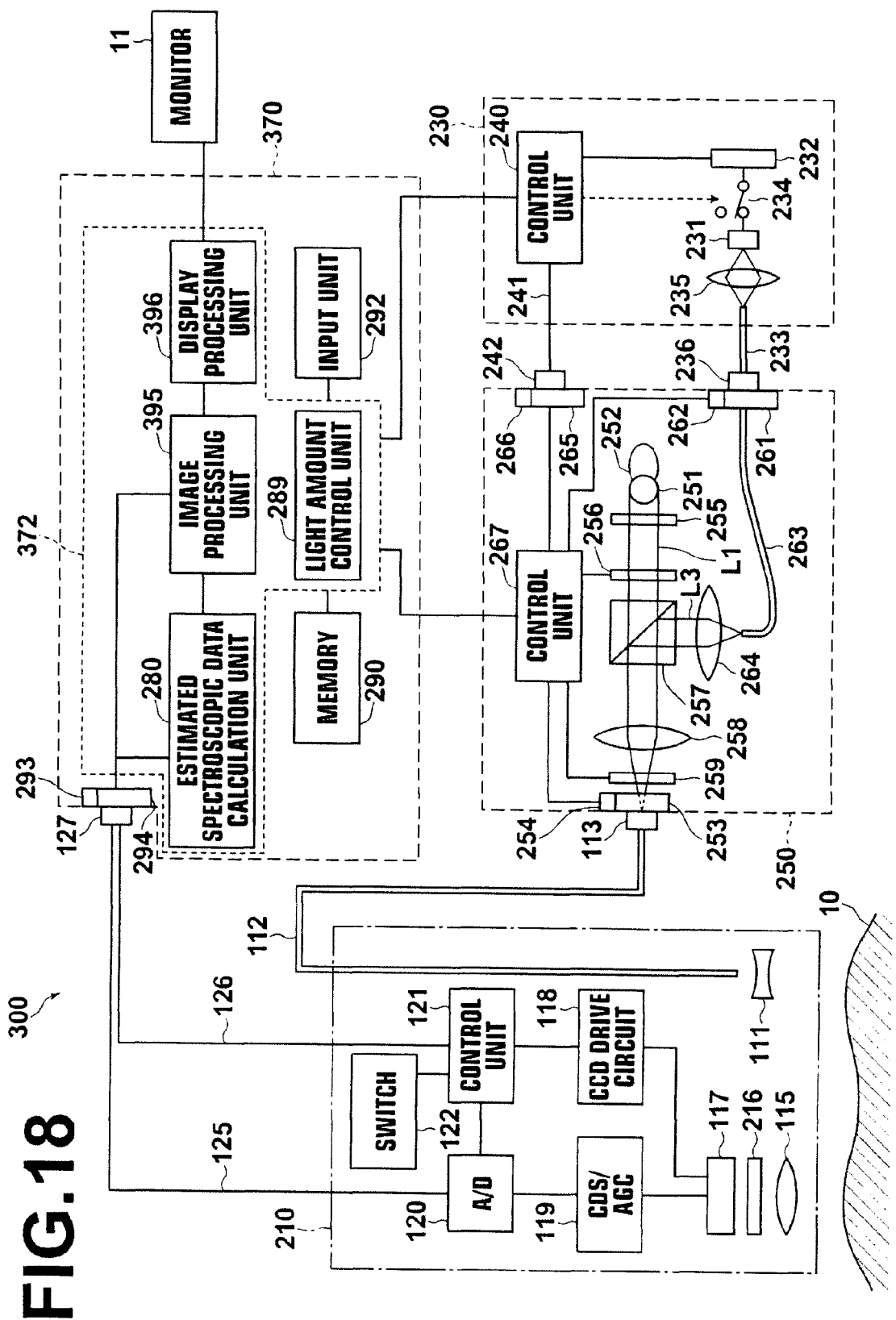
FIG. 18 is a block diagram of another fluorescence endoscope apparatus, illustrating the configuration thereof.

In the present embodiment, ordinary image processing unit 274 and display processing unit 276 that perform signal processing when the ordinary image mode is selected, and estimated spectroscopic data calculation unit 280, image processing unit 281, and display processing unit 288 that perform signal processing when the fluorescence image mode is selected are provided in processor 272, but the configuration of processor 272 is not limited to this. For example, processor 372 having estimated spectroscopic data calculation unit 280, image processing unit that functions as ordinary image processing unit 274 and image processing unit 281, and display processing unit 396 that functions as display processing unit 276 and display processing unit 288, as fluorescence image obtaining apparatus shown in FIG. 18. In this case, the signal outputted from scope unit 210 is inputted to image processing unit 395 when the ordinary image mode is selected, while it is inputted to estimated spectroscopic data calculation unit 280 and image processing unit 395 when the fluorescence image mode is selected.

Further, in the present embodiment, a wavelength range of a predetermined width including 490 nm of the center frequency of fluorescence is used as the particular fluorescence wavelength range, but it is not limited to this. That is, any wavelength range may be used as long as it is capable of substantially reflecting fluorescence intensities, and it may be, for example, a wavelength range from 485 to 495 nm. Preferably, the entirety of the particular fluorescence wavelength range is substantially a fluorescence wavelength range, and an unnecessarily wide wavelength range is undesirable. More specifically, it is preferable that the wavelength bandwidth is not greater than 100 nm, and more preferably not greater than 50 nm.

Figure 19:
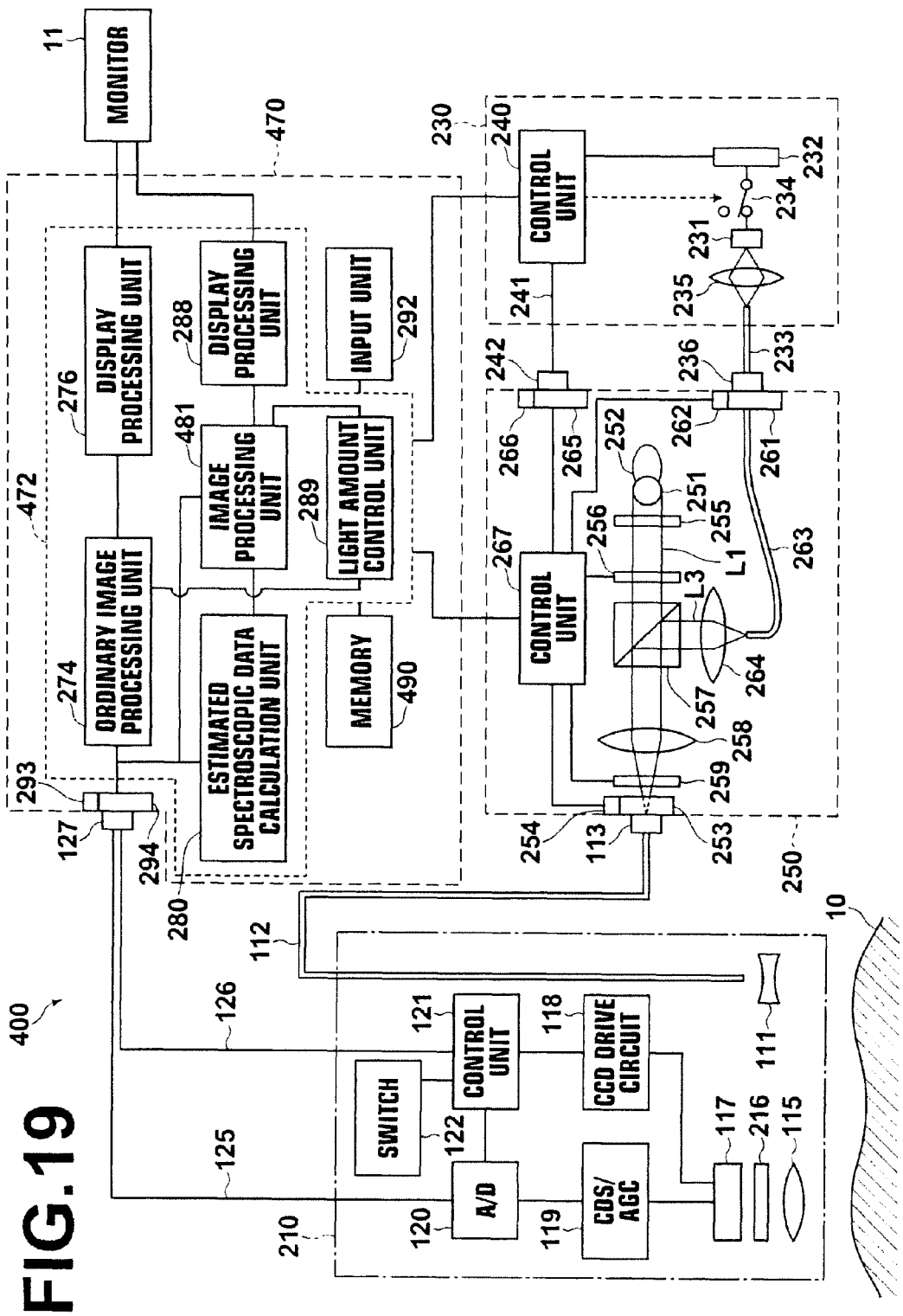
FIG. 19 is a block diagram of a fluorescence endoscope system according to a third embodiment of the present invention, illustrating the configuration thereof.

Next, a third embodiment of the present invention will be described with reference to FIGS. 19 to 21. FIG. 19 illustrates a schematic configuration of a fluorescence endoscope system 400 according to a third embodiment to which a fluorescence image obtaining apparatus of the present invention is applied. Components identical to those of fluorescence endoscope system 200 according to the second embodiment shown in FIG. 13 are given the same reference numerals and will not be elaborated upon further here.

Processor unit 470 includes processor 472. Processor 472 includes ordinary image processing unit 274 and display processing unit 276 that perform signal processing when the ordinary image mode is selected, estimated spectroscopic data calculation unit 280, image processing unit 481, and display processing unit 288 when the fluorescence image mode is selected, and light amount control unit 289 that controls the intensities of illumination light and excitation light.

Figure 20:
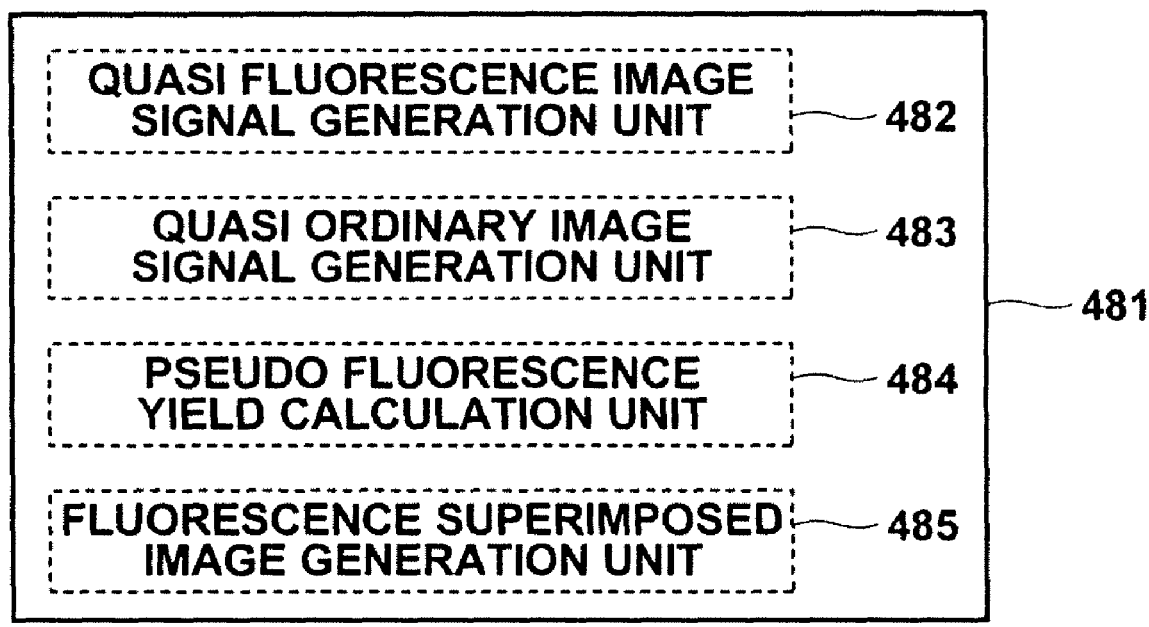
FIG. 20 is a block diagram of the image processing unit, illustrating the configuration thereof.

As shown in FIG. 20, image processing unit 481 includes quasi fluorescence image signal generation unit 482, quasi ordinary image signal generation unit 483, pseudo fluorescence yield calculation unit 484 and fluorescence superimposed image generation unit 485. Quasi fluorescence image signal generation unit 482, quasi ordinary image signal generation unit 483, pseudo fluorescence yield calculation unit 484 and fluorescence superimposed image generation unit 485 will be described in detail later.

Memory 490, keyboard type input unit 292, and connector 294 removably connected to connector 127 of scope unit 210 are connected to processor 472. Further, processor 472 is connected to control unit 121 of scope unit 210, control unit 267 of illumination light unit 250, and control unit 240 of excitation light unit 230.

Memory 490 has estimated matrix data, stored in advance as a table, for calculating estimated spectroscopic data of observation target 10. Further, the relationship between the emission intensity information of fluorescence emitted from a plurality of observation samples having substantially an identical fluorescence property to that of the observation target and emits fluorescence of different intensities and image signals obtained by imaging fluorescence emitted from the plurality of observation samples by a fluorescence endoscope system having an identical spectroscopic property to that of the fluorescence endoscope system used in the present embodiment is stored in memory 490 in advance as a lookup table. The lookup table will be described in detail later.

An operation of the fluorescence endoscope system 400 of the present embodiment structured in the manner as described above will now be described. An operation of the fluorescence endoscope system in the ordinary image mode is identical to that of fluorescence endoscope system 200 according to the second embodiment, so that it will not be elaborated upon further here.

When the endoscope system is operated in the ordinary image mode, a predetermined key of input unit 292 or switch 122 is depressed once by the user, the operation in the fluorescence image mode is started, and illumination light L1 and excitation light L3 are emitted onto observation target 10. The imaged signal outputted from CCD 117 is inputted to estimated spectroscopic data calculation unit 280 and image processing unit 481 of processor 472 of processor unit 470 as RGB image signals.

Pseudo fluorescence yield calculation unit 484 of image processing unit 481 calculates pseudo fluorescence intensity D by adding up each of estimated spectroscopic data q13 to q21 in a particular fluorescence wavelength range (470 to 510 nm). Further, the light intensity of image signal R outputted from scope unit 210 is used as reference light intensity E. Pseudo fluorescence yield F is obtained by dividing pseudo fluorescence intensity D by the value of light intensity of image signal R and outputted to fluorescence superimposed image generation unit 485. Further, reference light intensity E and pseudo fluorescence yield F are outputted to quasi fluorescence image signal generation unit 482 and quasi ordinary image signal generation unit 483.

Fluorescence superimposed image generation unit 485, for example, allocates green to pseudo fluorescence yield F if it is greater than a predetermined judgment value or allocates red if it is smaller than the predetermined judgment value, thereby generating a fluorescence image, as in the second embodiment. Further, fluorescence superimposed image generation unit 485 generates fluorescence superimposed image data in which the fluorescence image is superimposed on an achromatic image reflecting only the light intensity of image signal R outputted from scope unit 210 so that the user may easily recognize the position of a diseased tissue in which pseudo fluorescence yield F becomes small and outputs the fluorescence superimposed image data to display processing unit 288.

In the mean time, the relationship between pseudo fluorescence yield F as the emission intensity information of fluorescence emitted from a plurality of observation samples that emits fluorescence of different intensities and image signals obtained by imaging fluorescence emitted from the plurality of observation samples by a fluorescence endoscope system having an identical spectroscopic property to that of the fluorescence endoscope system used in the present embodiment is stored in memory 490 in advance as a lookup table like that shown in FIG. 21.

When generating the lookup table, multiple observation samples that emit fluorescence of different intensities are provided. Preferably, each observation sample has a spectral reflectivity and a spectral emissivity of fluorescence substantially identical to those of observation target 10. First, the distance between an observation sample and the tip of scope unit 210 is set to a shortest distance in which an image can be obtained, then illumination light L1 and excitation light L3 are emitted onto the observation sample to obtain an image formed of reflection light and fluorescence light in the same manner as described above, and pseudo fluorescence yield F and reference light intensity E (light intensity of R image signal) of a predetermined pixel. Thereafter, only excitation light L3 is emitted onto the observation sample to obtain an image of fluorescence emitted from the observation sample irradiated with excitation light L3 and an image signal (R, G, B) of fluorescence is obtained. Then, image signal (R, G, B) of the fluorescence at, for example, five different reference light intensities E1 to E5 are obtained by changing the distance between the observation sample and the tip of the scope unit. Influence on pseudo fluorescence yields F arising from the difference in distance between the observation sample and scope unit 210 is offset, since divisions by reference light intensities are performed for obtaining pseudo fluorescence yields F.

Pseudo fluorescence yield F is obtained from another observation sample having a different fluorescence emission intensity, i.e. from another observation sample having different pseudo fluorescence yield F in the same manner as described above. Then, reference light intensity E is changed in five steps, E1 to E5, to obtain an image signal (R, G, B) at each step. Likewise, from observation samples having different pseudo fluorescence yields F, for example, F1, F2, F3, F4, and F5, a fluorescence image signal (R, G, B) is obtained at each reference light intensity E. The results of these are stored in memory 490 in advance as the lookup table shown in FIG. 21. The lookup table may be generated by appropriately performing an averaging procedure, an interpolation operation, or the like on the measured pseudo fluorescence yield F, reference light intensity F, and fluorescence image signal (R, G, B).

Quasi fluorescence image signal generation unit 482 of image processing unit 481 obtains, with respect to each pixel, a fluorescence image signal (R, G, B) included in the image signal of each pixel using calculated pseudo fluorescence yield F and reference light intensity E, and the lookup table stored in memory 490, and outputs the obtained signals to quasi ordinary image signal generation unit 483. For example, if pseudo fluorescence yield F is F3 and reference light intensity E is E3, the fluorescence image signal is ($R_{33}$, $G_{33}$, $B_{33}$)

Quasi ordinary image signal generation unit 483 subtracts, with respect to each pixel, the fluorescence image signal ($R_{33}$, $G_{33}$, $B_{33}$) from the image signal (R, G, B) obtained by CCD 117 to generate a quasi ordinary image signal (R-$R_{33}$, G-$G_{33}$, B-$B_{33}$). Further, quasi ordinary image signal generation unit 483 performs various types of image processing on the three color image signals, generates a Y/C signal constituted by luminance signal Y and chrominance signals C, and outputs the Y/C signal to display processing unit 288.

Display processing unit 288 generates a display image in which a fluorescence enhanced image generated from the image signal Y/C for fluorescence enhanced image outputted from fluorescence superimposed image generation unit 485 and a quasi color ordinary image generated from the image signal Y/C for quasi ordinary image outputted from quasi ordinary image signal generation unit 483 are arranged side by side, and outputs the display image to monitor 11 for display.

As clear from the description above, in fluorescence endoscope system 400 according to the present invention, a lookup table representing the relationship between the pseudo fluorescence yield of fluorescence emitted from each of a plurality of observation samples that emit fluorescence of different emission intensities and the image signals of the fluorescence is stored in memory 490 in advance. Then, illumination light and excitation light are emitted onto observation target 10 to pick up an image faulted of reflection light of the illumination light and fluorescence emitted by the excitation of the excitation light, and, with respect to each pixel of picked up image signal, estimated spectroscopic data in a particular fluorescence wavelength range that includes a substantial center wavelength of the fluorescence are calculated from the image signal of each pixel and estimated matrix data stored in memory 490 for calculating estimated spectroscopic data. Further, pseudo fluorescence intensity D and reference light intensity E are obtained from the estimated spectroscopic data in the particular fluorescence wavelength range, then pseudo fluorescence yield F is calculated by dividing pseudo fluorescence intensity D by reference light intensity E, and an image signal of relevant fluorescence is obtained from pseudo fluorescence yield F and the lookup table stored in memory 490. The image signal of relevant fluorescence is subtracted from the image signal obtained by CCD 117 to generate a quasi ordinary image signal, so that the quasi ordinary image signal has a very low content rate of fluorescence image signal and a quasi ordinary image generated from the quasi ordinary image signal may be used as the substitute of an ordinary image obtained by emitting only illumination light. Further, the number of frames of quasi ordinary image which may be obtained per unit time is not reduced, so that even when the quasi ordinary image is displayed as a moving picture, a favorable image may be provided.

Further, in the third embodiment, a wavelength range of a predetermined width including 490 nm of the center frequency of fluorescence is used as the particular fluorescence wavelength range, but it is not limited to this, as in the second embodiment. That is, any wavelength range may be used as long as it is capable of substantially reflecting fluorescence intensities, and it may be, for example, only 490 nm, 480 nm, or 500 nm. Otherwise, it may be a wavelength range from 485 to 495 nm, or the like. For example, when the particular fluorescence wavelength range is only 490 nm, a pseudo fluorescence intensity can be obtained by calculating only estimated spectroscopic data (q17), while if the particular fluorescence wavelength range is from 485 to 495 nm, a pseudo fluorescence intensity can be obtained by calculating estimated spectroscopic data (q16, q17, and q18). The wavelength bandwidth of the particular fluorescence wavelength range is similar to that of the second embodiment.

In the present embodiment, a lookup table indicating the relationship between the pseudo fluorescence yield of fluorescence and the image signal of the fluorescence is stored in memory 490. But, instead of this lookup table, a lookup table that indicates the relationship between the intensity of fluorescence and the image signal of the fluorescence may be stored in memory 490 in advance. For example, where each area of an observation target is equidistant from scope unit 210, a fluorescence image signal may be calculated using the fluorescence intensity instead of the pseudo fluorescence yield.

Further, in the second and third embodiments, the description has been made using a fluorescence endoscope system in which illumination light L1 and excitation light L3 propagated through scope unit 210 are emitted onto observation target 10 simultaneously, then estimated spectroscopic data are calculated using an image signal obtained by CCD 117 and estimated matrix data stored in a memory in advance, a pseudo fluorescence intensity is calculated from the estimated spectroscopic data, and a fluorescence image is generated based on the pseudo fluorescence intensity. But the embodiment of the fluorescence image obtaining apparatus of the present invention is not limited to that described above. That is, the invention may take any form as long as it obtains an image by emitting illumination light and excitation light. The light source of the auxiliary light may be an LED. The invention is applicable, for example, to an endoscope system having a light source unit of LED or the like at the tip of scope unit 210, colposcope, capsule endoscope system, or the like. Otherwise, it may be a microscope having image acquisition capabilities or the like.

Further, primary three-color filter is described as the mosaic filter of CCD 117, but the type of filter is not limited to this, and a four color mosaic filter, complementary mosaic filter, or the like may also be used. In such a case, a signal outputted from CCD 117 may be converted to a primary color signal by signal processing or estimated matrix data based on the spectroscopic properties of these mosaic filters may be stored in a memory in advance.

What is claimed is:

1. An image obtaining method, comprising:
   obtaining an image of an observation target irradiated with illumination light and excitation light simultaneously, the image being formed of reflection light of the illumination light reflected from the observation target and fluorescence emitted from the observation target excited by the excitation light;
   calculating, with respect to each pixel of an obtained image signal, estimated spectroscopic data in a particular fluorescence wavelength range which comprises a wavelength range that includes at least a substantial center wavelength of the fluorescence from an image signal of each pixel and estimated matrix data stored in advance for calculating estimated spectroscopic data;
   obtaining a quasi fluorescence image signal that includes an image signal attributable to the fluorescence based on the estimated spectroscopic data in the particular fluorescence wavelength range; and
   generating a quasi ordinary image signal by subtracting the quasi fluorescence image signal from the obtained image signal.

2. An image obtaining apparatus, comprising:
   a light emitting unit for emitting illumination light and excitation light onto an observation target simultaneously;
   an imaging unit for obtaining an image formed of reflection light of the illumination light reflected from the observation target and fluorescence emitted from the observation target irradiated with the excitation light;
   a first storage unit for storing estimated matrix data for calculating estimated spectroscopic data;
   an estimated spectroscopic data calculation unit for calculating, with respect to each pixel of the image signal outputted from the imaging unit, estimated spectroscopic data in a particular fluorescence wavelength range which comprises a wavelength range including at least a substantial center wavelength of the fluorescence using an image signal of each pixel and the estimated matrix data;
   an image processing unit comprising a quasi fluorescence image signal generation unit for generating a quasi fluorescence image signal that includes an image signal attributable to the fluorescence based on the estimated spectroscopic data in the particular fluorescence wavelength range calculated by the estimated spectroscopic data calculation unit; and
   a quasi ordinary image signal generation unit for generating a quasi ordinary image signal by subtracting the quasi fluorescence image signal from the image signal obtained by the imaging unit.

3. The image obtaining apparatus of claim 2, wherein the image processing unit comprises a fluorescence emission intensity information calculation unit for obtaining fluorescence emission intensity information, which comprises information reflecting an emission intensity of the fluorescence emitted from the observation target, from the estimated spectroscopic data in the particular fluorescence wavelength ranger,
   wherein the apparatus further includes a second storage unit for storing, in advance, a relationship between fluorescence emission intensity information of fluorescence emitted from a plurality of observation samples and fluorescence image signals obtained by imaging the fluorescence emitted from the plurality of observation samples by the imaging unit, the plurality of observation samples having a fluorescence property substantially identical to that of the observation target and emitting fluorescence of different emission intensities when irradiated with the excitation light, and
   wherein the quasi fluorescence image signal generation unit comprises a unit that generates the quasi fluorescence image signal based on the fluorescence emission intensity information obtained by the fluorescence emission intensity information calculation unit and the relationship stored in the second storage unit.

4. The image obtaining apparatus of claim 3, wherein the light emitting unit comprises a unit that emits reference light having a wavelength range different from that of the excitation light onto the observation target simultaneously with an emission of the excitation light,
   wherein the imaging unit comprises a unit that obtains an image that includes reflection light of the reference light reflected from the observation target, and
   wherein the fluorescence emission intensity information calculation unit comprises a unit that calculates a reference light intensity, which comprises an intensity of the reflection light of the reference light obtained by the imaging unit, calculates a pseudo fluorescence intensity, which comprises a light intensity in the particular fluorescence wavelength range from the estimated spectroscopic data in the particular fluorescence wavelength range, and calculates a pseudo fluorescence yield obtained by diving the pseudo fluorescence intensity by the reference light intensity as the fluorescence emission intensity information.

5. The image obtaining apparatus of claim 2, further comprising an input unit for setting the particular fluorescence wavelength range by an input operation.